US007524647B2

(12) United States Patent
Schultz et al.

(10) Patent No.: US 7,524,647 B2
(45) Date of Patent: *Apr. 28, 2009

(54) SITE SPECIFIC INCORPORATION OF KETO AMINO ACIDS INTO PROTEINS

(75) Inventors: Peter G. Schultz, La Jolla, CA (US); Lei Wang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 46 days.

This patent is subject to a terminal disclaimer.

(21) Appl. No.: 11/978,160

(22) Filed: Oct. 26, 2007

(65) Prior Publication Data

US 2008/0176284 A1 Jul. 24, 2008

Related U.S. Application Data

(63) Continuation of application No. 10/530,421, filed as application No. PCT/US03/32576 on Oct. 15, 2003.

(60) Provisional application No. 60/419,265, filed on Oct. 16, 2002, provisional application No. 60/420,990, filed on Oct. 23, 2002.

(51) Int. Cl.
  C12P 21/06 (2006.01)
  C12N 9/22 (2006.01)
  C12N 15/87 (2006.01)
(52) U.S. Cl. .............. 435/69.1; 435/91.2; 435/483; 435/440; 435/419; 435/455; 530/350
(58) Field of Classification Search .............. None
  See application file for complete search history.

(56) References Cited

U.S. PATENT DOCUMENTS

| 6,927,042 B2 | 8/2005 | Schultz et al. |
| 7,045,337 B2 | 5/2006 | Schultz et al. |
| 7,083,970 B2 | 8/2006 | Schultz et al. |

FOREIGN PATENT DOCUMENTS

| WO | WO 02/085923 | 10/2002 |
| WO | WO 02/086075 | 10/2002 |

OTHER PUBLICATIONS

Bradley et al. "tRNA2Gln Su+2 mutants that increase amber suppression." *J. Bacteriol.* 145(2):704-712 (1981).
Jeruzalmi & Steitz. "Structure of T7 RNA polymerase complexed to the transcriptional inhibitor T7 lysozyme." *EMBO J.*, 17(14):4101-4113 (1998).
Turcatti et al. "Probing the Structure and Function of the Tachykinin Neurokinin-2 Receptor through Biosynthetic Incorporation of Fluorescent Amino Acids at Specific Sites." *J. Biol. Chem.*, 271(33):19991-19998 (1996).
Altenbach et al. "Transmembrane Protein Structure: Spin Labeling of Bacteriorhodopsin Mutants." *Science* 248(4959):1088-92 (1990).
Anderson et al. "Exploring the Limits of Codon and Anticodon Size." *Chemistry and Biology*, 9(2):237-244 (2002).
Azoulay et al. "Glutamine analogues as Potential Antimalarials." *Eur. J. Med. Chem.* 26, 201-5 (1991).
Bain et al. "Biosynthetic site-specific Incorporation of a non-natural amino acid into a polypeptide." *J. Am. Chem. Soc.*, 111(20):8013-8014 (1989).
Barton et al. "Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives." *Tetrahedron Lett.* 43, 4297-4308 (1987).
Begley et al. *Topics in Curr. Chem.*, eds. Leeper, F. J. & Vederas, J. C. (Springer-Verlag, New York), 195:93-142 (1997).
Bock et al. "Selenocysteine: the 21st amino acid." *J. Mol. Microbiol.* 5(3):515-520 (1991).
Boles et al. "Bio-incorporation of telluromethionine into buried residues of dihydrofolate reductase." *Nat. Struct. Biol.*, 1(5):283-284 (1994).
Brick et al. "Structure of tyrosyl-tRNA synthetase refined at 2.3 A resolution. Interaction of the enzyme with the tyrosyl adenylate intermediate." *J. Mol. Biol.*, 208:83-98 (1989).
Brunner, "New Photolabeling and Crosslinking Methods." *Annu. Rev. Biochem.*, 62:483-514 (1993).
Budisa et al. "Bioincorporation of telluromethionine into proteins: a promising new approach for X-ray structure analysis of proteins." *J. Mol. Biol.*, 270(4):616-623 (1997).
Budisa et al. "Residue-specific bioincorporation of non-natural, biologically active amino acids into proteins as possible drug carriers: Structure and stability of the per-thiaproline mutant of annexin V." *PNAS*, 95(2):455-459 (1998).
Budisa et al. "Toward the experimental codon reassignment in vivo: protein building with an expanded amino acid repertoire." *FASEB J.* 13(1):41-51 (1999).
Budisa et al. "High-level biosynthetic substitution of methionine in proteins by its analogs 2-aminohexanoic acid, selenomethionine, telluromethionine and ethionine in *Escherichia coli*." *Eur. J. Biochem.*, 230(2):788-796 (1995).
Bult et al. "Complete Genome Sequence of the Methanogenic archaeon, *Methanococcus jannaschii*," Methanocaldococcus jannaschii DSM 2661, section 33 of 150 of the complete genome, GenBank Accession No. AAB98375 (Jun. 2, 2004).
Bult et al. "Complete Genome Sequence of the Methanogenic archaeon, *Methanococcus jannaschii*," Methanocaldococcus jannaschii DSM 2661, complete genome, GenBank Accession No. AAB98375 (Dec. 20, 2005).

(Continued)

Primary Examiner—Andrew D Kosar
Assistant Examiner—Kagnew H Gebreyesus
(74) Attorney, Agent, or Firm—Quine Intellectual Property Law Group; Gary Baker

(57) ABSTRACT

Compositions and methods of producing components of protein biosynthetic machinery that include orthogonal tRNAs, orthogonal aminoacyl-tRNA synthetases, and orthogonal pairs of tRNAs/synthetases, which incorporate keto amino acids into proteins are provided. Methods for identifying these orthogonal pairs are also provided along with methods of producing proteins with keto amino acids using these orthogonal pairs.

7 Claims, 9 Drawing Sheets

OTHER PUBLICATIONS

Chin et al. "Addition of a photocrosslinking amino acid to the genetic code of *Escherichia coli*." *PNAS*, 99(17):11020-11024 (2002).
Chin et al. "An Expanded Eukaryotic Genetic Code." *Science*, 301(5635):964-967 (2003).
Chin et al. "Addition of p-Azido-L-phenylalanine to the genetic code of *Escherichia coli*." *J Am Chem Soc* 124:9026-9027 (2002).
Christie & Rapoport. "Synthesis of Optically Pure Pipecolates from L-Asparagine. Application to the Total Synthesis of (+)-Apovincamine through Amino Acid Decarbonylation and Iminium Ion Cyclization." *J. Org. Chem*. 50(8):1239-1246 (1985).
Cornish et al. "Probing Protein Structure and Function with an Expanded Genetic Code." *Agnew. Chem. Int. Ed. Engl*., 34(6):621-633 (1995).
Cornish et al. "Site-Specific Protein Modification Using a Ketone Handle." *J. Am. Chem. Soc*. 118(34):8150-8151 (1996).
Craig et al. "Absolute Configuration of the Enantiomers of 7-Chloro-4 [[4-(diethylamino)-1-methylbutyl]amino]quinoline (Chloroquine)." *J. Org. Chem*. 53:1167-1170 (1988).
Creighton. "Disulfide bonds as probes of protein folding pathways." *Methods Enzymol*. 131:83-106 (1986).
Cropp et al. "An Expanding Genetic Code." *Trends in Genetics*, 20(12):625-630 (2004).
Diaz et al. "Biodegradation of Aromatic Compounds by *Escherichia coli*." *Microbiol. Mol. Biol. Rev*. 65(4):523-569 (2001).
Doctor & Mudd, "Species Specificity of Amino Acid Acceptor Ribonucleic Acid and Aminoacyl Soluble Ribonucleic Acid Synthetases" *J. Biol. Chem*., 238(11):3677-3681 (1963).
Doring et al. "Enlarging the Amino Acid Set of *Escherichia coli* by Infiltration of the Valine Coding Pathway *Science*." 292:501 (2001).
Dougherty. "Unnatural amino acids as probes of protein structure and function." *Curr. Opin. Chem. Biol*., 4(6):645-652 (2000).
Duewel et al. "Incorporation of trifluoromethionine into a phage lysozyme: implications and a new marker for use in protein 19F NMR." *Biochemistry*, 36(11):3404-3416 (1997).
Dunten & Mowbray. "Crystal structure of the dipeptide binding protein from *Escherichia coli* involved in active transport and chemotaxis." *Protein Science* 4 (11):2327-2334 (1995).
Ellman et al. "Biosynthetic method for introducing unnatural amino acids site-specifically into proteins." *Methods in Enzymol*., 202:301-336 (1992).
Ellman et al. "Site-specific incorporation of novel backbone structures into proteins." *Science*, 255:197-200 (1992).
England et al. "Backbone Mutations in Transmembrane Domains of a Ligand-Gated Ion Channel: Implications for the Mechanism of Gating." *Cell*, 96(1):89-98 (1999).
Fechter et al. "Major tyrosine identity determinants in *Methanococcus jannaschii* and *Saccharomyces cerevisiae* tRNAT yr are conserved but expressed differently." *Eur. J. Biochem*. 268(3):761-767 (2001).
Feng et al. "Expanding tRNA recognition of a tRNA synthetase by a single amino acid change." *PNAS* 100(10): 5676-5681 (2003).
Forster et al. "Programming peptidomimetic synthetases by translating genetic codes designed de novo." *PNAS* 100(11):6353-6357 (2003).
Francisco et al. (1993) "Production and fluorescence-activated cell sorting of *Escherichia coli* expressing a functional antibody fragment on the external surface." *PNAS* 90:10444-8.
Francklyn et al. "Aminoacyl-tRNA synthetases: Versatile players in the changing theater of translation." *RNA*, 8(11):1363-1372 (2002).
Friedman & Chatterrji. "Synthesis of Derivatives of Glutamine as Model Substrates for Anti-Tumor Agents." *J. Am. Chem. Soc*. 81(14):3750-3752 (1959).
Furter. "Expansion of the genetic code: site-directed p-fluorophenylalanine incorporation in *Escherichia coli*." *Protein Sci*., 7(2):419-426 (1998).
Gabriel & McClain. "A set of plasmids constitutively producing different RNA levels in *Escherichia coli*." *J. Mol. Biol*. 290:385-389 (1999).
Gaietta et al. "Multicolor and electron microscopic imaging of connexin trafficking." *Science* 296(5567):503-507 (2002).

Gallivan et al. "Site-specific incorporation of biotinylated amino acids to identify surface-exposed residues in integral membrane proteins." *Chem. Biol*., 4(10):739-749 (1997).
Gay et al. "Modification of the amino acid specificity of tyrosyl-tRNA synthetase by protein engineering." *FEBS Lett*. 318(2):167-171 (1993).
GenBank Accession No. E64348, Bult et al. 'Complete genome sequence of the *Methanogenic archaeon, Methanococcus jannaschii*,' Gene Sequence, Jun. 3, 1996.
GenBank Accession No. Q57834, publication date Oct. 16, 2001, date of retrieval Oct. 6, 2003.
Geoghegan & Stroh. "Site-directed conjugation of nonpeptide groups to peptides and proteins via periodate oxidation of a 2-amino alcohol. Application to modification at N-terminal serine." *Bioconjug. Chem*. 3(2):138-146 (1992).
Giegé et al. "Universal rules and idiosyncratic features in tRNA identity," *Nucleic Acids Res*. 26(22):5017-5035 (1998).
Giegé et al. "Aspartate identity of transfer RNAs." *Biochimie*, 78(7):605-623 (1996).
Giuliano et al. "Fluorescent protein biosensors: measurement of molecular dynamics in living cells." *Annu. Rev. Biophys. Biomol. Struct*. 24:405-434 (1995).
Griffin et al. "Specific Covalent Labeling of Recombinant Protein Molecules Inside Live Cells." *Science* 281:269-272 (1998).
Guckian & Kool. "Highly Precise Shape Mimicry by a Difluorotoluene Deoxynucleoside, a Replication-Competent Substitute for Thymidine." *Angew. Chem. Int. Ed. Engl*., 36(24):2825-2828 (1997).
Hamano-Takaku et al. "A Mutant *Escherichia coil* Tyrosyl-tRNA Synthetase Utilizes the Unnatural Amino Acid Azatyrosine More Efficiently than Tyrosine." *J. Biol. Chem*., 275(51):40324-40328 (2000).
Hao et al. "A New UAG-Encoded Residue in the Structure of a Methanogen Methyltransferase." *Science* 296(5572):1462-1466 (2002).
He et al. "The gene cluster for chloramphenicol biosynthesis in Streptomyces venezuelae ISP5230 includes novel shikimate pathway homologues and a monomodular non-ribosomal peptide synthetase gene." *Microbiology*, 147(10):2817-2829 (2001).
Hendrickson et al. "Selenomethionyl proteins produced for analysis by multiwavelength anomalous diffraction (MAD): a vehicle for direct determination of three-dimensional structure." *EMBO J*., 9(5):1665-1672 (1990).
Hirao et al. "An unnatural base pair for incorporating amino acid analogues into protein," *Nature Biotechnology*, 20(2):177-182 (2002).
Hohsaka et al. (1999) "Efficient Incorporation of Nonnatural Amino Acids with Large Aromatic Groups into Streptavidin in In Vitro Protein Synthesizing Systems." *J. Am. Chem. Soc*., 121(1):34-40.
Hohsaka et al. "Efficient Incorporation of Nonnatural Amino Acids with Large Aromatic Groups into Streptavidin in In Vitro Protein Synthesizing Systems." *J. Am. Chem. Soc*., 121(1):34-40 (1999).
Hohsaka et al. "Incorporation of Two Different Nonnatural Amino Acids Independently into a Single Protein through Extension of the Genetic Code." *J. Am. Chem. Soc*., 121(51): 12194-12195 (1999).
Ibba & Hennecke. "Relaxing the substrate specificity of an aminoacyl-tRNA synthetase allows in vitro and in vivo synthesis of proteins containing unnatural amino acids." *FEBS Lett*., 364(3):272-275 (1995).
Ibba et al. "Substrate specificity is determined by amino acid binding pocket size in *Escherichia coli* phenylalanyl-tRNA synthetase." *Biochemistry*, 33(23):7107-7112 (1994).
Ibba. "Strategies for in vitro and in vivo translation with non-natural amino acids." Biotechnol Gente Eng. Rev. 13:197-216 (1996).
Jakubowski & Goldman. "Editing of errors in selection of amino acids for protein synthesis," *Microbiol. Rev*., 56(3):412-429 (1992).
Jucovic And Hartley. (1996) "Protein-protein interaction: a genetic selection for compensating mutations at the barnase-barstar interface." *PNAS*, 93(6):2343-2347.
Kiga et al. (2002) "An engineered *Escherichia coli* tyrosyl-tRNA synthetase for site-specific incorporation of an unnatural amino acid into proteins in eukaryotic translation and its application in a wheat germ cell-free system." *PNAS*, 99(15):9715-9720.

Kiick & Tirrell. "Protein Engineering by In Vivo Incorporation of Non-Natural Amino Acids: Control of Incorporation of Methionine Analogues by Methionyl-tRNA Synthetase," *Tetrahedron*, 56(48):9487-9493 (2000).

King and Kidd. "A New Synthesis of Glutamine and of γ-Dipeptides of Glutamic Acid from Phthylated Intermediates." *J. Chem. Soc.*, 4:3315-3319 (1949).

Kleeman et al. "Human Tyrosyl-tRNA Synthetase Shares Amino Acid Sequence Homology with a Putative Cytokine" *J. Biol. Chem.*, 272(22):14420-14425 (1997).

Kleina et al. "Construction of *Escherichia coli* amber suppressor tRNA genes. II. Synthesis of additional tRNA genes and improvement of suppressor efficiency." *J. Mol. Biol.* 213(4):705-717 (1990).

Kool. "Synthetically modified DNAs as substrates for polymerases," *Curr. Opin. Chem. Biol.*, 4(6):602-608 (2000).

Koskinen & Rapoport. "Synthesis of 4-Substituted Prolines as Conformationally Constrained Amino Acid Analogues." *J. Org. Chem.* 54(8):1859-1866. (1989).

Kowal & Oliver. "Exploiting unassigned codons in *Micrococcus luteus* for tRNA-based amino acid mutagenesis." *Nucl. Acid. Res.*, 25(22):4685-4689 (1997).

Kowal et al. "Twenty-first aminoacyl-tRNA synthetase-suppressor tRNA pairs for possible use in site-specific incorporation of amino acid analogues into proteins in eukaryotes and in eubacteria." *Proc. Natl. Acad. Sci. USA*, 98(5):2268-2273 (2001).

Krieg et al., "Photocrosslinking of the signal sequence of nascent preprolactin of the 54-kilodalton polypeptide of the signal recognition particle," *Proc. Natl. Acad. Sci*, 83(22):8604-8608 (1986).

Kwok & Wong. "Evolutionary relationship between Halobacterium cutirubrum and eukaryotes determined by use of aminoacyl-tRNA synthetases as phylogenetic probes." *Can. J. Biochem.*, 58(3):213-218 (1980).

Lee and Xun. "Novel Biological Process for L-DOPA Production from L-Tyrosine by P-Hydroxyphenylacetate 3-Hydroxylase," *Biotechnology Letters*, 20(5):479-482, (1998).

Liu & Schultz. (1999) "Progress toward the evolution of an organism with an expanded genetic code." *PNAS*, 96(9):4780-4785.

Liu et al. (1997) "Engineering a tRNA and aminoacyl-tRNA synthetase for the site-specific incorporation of unnatural amino acids into protein in vivo." *PNAS*, 94(19):10092-10097.

Liu et al. "Characterization of an 'orthogonal' suppressor tRNA derived from *E. coli* tRNA$_2^{Gln}$" *Chem. Biol.*, 4:685-691 (1997).

Lorincz et al. "Enzyme-generated intracellular fluorescence for single-cell reporter gene analysis utilizing *Escherichia coli* beta-glucuronidase." *Cytometry*, 24(4):321-329 (1996).

Lu et al. "Probing ion permeation and gating in a K+ channel with backbone mutations in the selectivity filter." *Nat. Neurosci.*, 4(3):239-246 (2001).

Ma et al. "In vitro protein engineering using synthetic tRNAAla with different anticodons." *Biochemistry*, 32(31):7939-7945 (1993).

Magliery et al. "Expanding the Genetic Code: Selection of Efficient Suppressors of Four-base Codons and Identification of "Shifty" Four-base Codons with a Library Approach in *Escherichia coli*," *J. Mol. Biol.*, 307(3): 755-769 (2001).

Mahal et al. "Engineering chemical reactivity on cell surfaces through oligosaccharide biosynthesis." *Science*, 276(5315):1125-1128 (1997).

Mannuzzu et al. "Direct Physical Measure of Conformational Rearrangement Underlying Potassium Channel Gating." *Science*, 271(5246):213-216 (1996).

Matsoukas et al. "Differences in Backkbone Structure between Angiotensin II Agonists and Type I Antagonists." *J. Med. Chem.*, 38(23): 4660-4669 (1995).

McMinn et al. "Efforts toward Expansion of the Genetic Alphabet: DNA Polymerase Recognition of a Highly Stable, Self-Pairing Hydrophobic Base," *J. Am. Chem. Soc.*, 121(49):11585-11586 (1999).

Meggers et al. "A Novel Copper-Mediated DNA Base Pair," *J. Am. Chem. Soc.*, 122(43):10714-10715 (2000).

Mendel et al. "Site-Directed Mutagenesis with an Expanded Genetic Code," *Annu. Rev. Biophys. Biomol. Struct.* 24:435-462 (1995).

Miller et al. "Flash decaging of tyrosine sidechains in an ion channel," *Neuron*, 20(4):619-624 (1998).

Minks et al. "Noninvasive tracing of recombinant proteins with fluorophenylalanine-fingers". *Anal. Biochem.*, 284(1):29-34 (2000).

Moore et al. "Quadruplet codons: implications for code expansion and the specification of translation step size." *J. Mol. Biol.*, 298(2):195-209 (2000).

Nickitenko et al. "2 A resolution structure of DppA, a periplasmic dipeptide transport/chemosensory receptor." *Biochemistry* 34(51):16585-16595 (1995).

Nilsson et al. "A synthetic IgG-binding domain based on *Staphylococcal* protein A." *Protein Eng.* 1(2):107-113 (1987).

Noren et al. (1989) "A general method for site-specific incorporation of unnatural amino acids into proteins." *Science*, 244(4901):182-188.

Nowak et al. "Nicotinic receptor binding site probed with unnatural amino acid incorporation in intact cells." *Science*, 268(5209):439-442 (1995).

Ogawa et al. "Efforts toward the Expansion of the Genetic Alphabet: Information Storage and Replication with Unnatural Hydrophobic Base Pairs." *J. Am. Chem. Soc.*, 122(14):3274-3287 (2000).

Ogawa et al. "Rational Design of an Unnatural Base Pair with Increased Kinetic Selectivity," *J. Am. Chem. Soc.*, 122(36):8803-8804 (2000).

Ohno et al. "Co-expression of yeast amber suppressor tRNATyr and tyrosyl-tRNA synthetase in *Escherichia coli*: possibility to expand the genetic code," J. Biochem. 124(6): 1065-1068 (1998).

Okeley. & Van Der Donk. "Novel cofactors via post-translational modifications of enzyme active sites." *Chem. Biol.* 7, R159-R171 (2000).

O'Mahony et al. (1989) "Glycine tRNA mutants with normal anticodon loop size cause 1 frameshifting." *PNAS*, 86(20):7979-7983.

Pastrnak & Schultz. "Phage selection for site-specific incorporation of unnatural amino acids into proteins in vivo." *Bioorg. Med. Chem.*, 9(9):2373-2379 (2001).

Pastrnak et al. "A new orthogonal suppressor tRNA/aminoacyl-tRNA synthetase pair for evolving an organism with an expanded genetic code." *Helv Chim Acta* 83:2277-2286 (2000).

Piccirilli et al. "Enzymatic incorporation of a new base pair into DNA and RNA extends the genetic alphabet," *Nature*, 343:33-37 (1990).

Saks et al. "An Engineered *Tetrahymena* tRNA$^{Gln}$ for in Vivo Incorporation of Unnatural Amino Acids into Proteins by Nonsense Suppression." J.Biol. Chem. 271(38): 23169-23175 (1996).

Santoro & Schultz. "Directed evolution of the site specificity of Cre recombinase." *Proc. Natl. Acad Sci USA*, 99(7):4185-4190 (2002).

Santoro et al. "An efficient system for the evolution of aminoacyl-tRNA synthetase specificity." *Nature Biotech*, 20:1044-1048.

Sayers et al. "5', 3' Exonuclease in phosphorothioate-based oligonucleotide-directed mutagenesis." *Nucleic Acids Res.*, 16(3):791-802 (1988).

Sharma et al. "Efficient introduction of aryl bromide functionality into proteins in vivo." *FEBS Lett.*, 467(1):37-40 (2000).

Sieber et al. "Libraries of hybrid proteins from distantly related sequences." *Nature Biotechnology*, 19:456-460 (2001).

Sprinzl et al. "Compilation of tRNA sequences and sequences of tRNA genes," *Nucleic Acids Res.* 26(1):148-153 (1998).

Srinivasan . & Krzycki. "Pyrrolysine Encoded by UAG in Archaea: Charging of a UAG-Decoding Specialized tRNA." *Science* 296(5572):1459-1462 (2002).

Steer & Schimmel. "Major anticodon-binding region missing from an archaebacterial tRNA synthetase." *J. Biol. Chem.* 274(50):35601-35606 (1999).

Subasinghe et al., "Quisqualic acid analogues: synthesis of beta-heterocyclic 2-aminopropanoic acid derivatives and their activity at a novel quisqualate-sensitized site." *J. Med. Chem.* 35(24):4602-4607 (1992).

Sussman et al. "Crystal structure of yeast phenylalanine transfer RNA. I. Crystallographic refinement," *J. Mol. Biol.* 123(4):607-630 (1978).

Switzer et al. "Enzymatic incorporation of a new base pair into DNA and RNA." *J. Am. Chem. Soc.*, 111(21):8322-8323 (1989).

Tae et al. "Efforts toward expansion of the genetic alphabet: replication of DNA with three base pairs," *J. Am. Chem. Soc.*, 123(30):7439-7440 (2001).

Tang et al. "Fluorinated Coiled-Coil Proteins Prepared In Vivo Display Enhanced Thermal and Chemical Stability." *Angew. Chem. Int. Ed. Engl.*, 40(8):1494-1496 (2001).

Van Hest & Tirrell. "Efficient introduction of alkene functionality into proteins in vivo." *FEBS Lett.*, 428(1-2):68-70 (1998).

Van Hest et al. "Efficient Incorporation of Unsaturated Methionine Analogues into Proteins in Vivo." *J. Am. Chem. Soc.*, 122(7):1282-1288 (2000).

Wakasugi et al. "Genetic code in evolution: switching species-specific aminoacylation with a peptide transplant." *EMBO J.* 17(1):297-305 (1998).

Wang & Schultz "A General Approach for the Generation of Orthogonal tRNAs," *Chem. Biol.* 8:883-890 (2001).

Wang & Schultz. "Expanding the genetic code," *Chem. Commun.*, 1:1-11 (2002).

Wang et al. "A new functional suppressor tRNA/aminoacyl-tRNA synthetase pair for the in vivo incorporation of unnatural amino acids into proteins," *J. Am. Chem. Soc.* 122:5010-5011 (2000).

Wang et al. "Addition of the keto functional croup to the genetic code of *Escherichia coli*." *PNAS*, 100(1):56-61 (2003).

Wang et al. (2002) "Adding L-3-(2-Naphthyl)alanine to the Genetic Code of *E. coli*," *J. Am. Chem. Soc*. 124:1836-1837.

Wang et al. (2004) "Expanding the genetic code." *Angew. Chem. Int. Ed.*, 44(1):34-66.

Wang et al. "Expanding the genetic code of *Escherichia coli*." *Science*, 292(5516):498-500 (2001).

Weiner et al. "A binding protein for L-glutamine and its relation to active transport in *E. coli*." *Archives of Biochemistry and Biophysics*, 124(2):715-717 (1971).

Whelihan & Schimmel. "Rescuing an essential enzyme-RNA complex with a non-essential appended domain." *EMBO J.*, 16(10):2968-2974 (1997).

Wu et al. "Studying organelle physiology with fusion protein-targeted avidin and fluorescent biotin conjugates," *Methods Enzymol*. 327:546-64 (2000).

Wu et al. "Enzymatic phosphorylation of unnatural nucleosides," *J. Am. Chem. Soc*. 124(49)14626-14630 (2002).

Yarus. "Translational efficiency of transfer RNA's: Use of an expanded anticodon." *Science* 218(4573):646-652 (1982).

Zhang et al. "The Selective Incorporation of Alkenes into Proteins in *Escherichia coli*." *Angew. Chem. Int. Ed. Engl.* 41(15):2840-2842 (2002).

Zlokarnik et al. "Quantitation of Transcription and Clonal Selection of Single Living Cells with B-Lactamase as Reporter." *Science*, 279(5347):84-88 (1998).

ently, it was

SEQUENCE LISTING

<160> NUMBER OF SEQ ID NOS: 24

<210> SEQ ID NO 1
<211> LENGTH: 918
<212> TYPE: DNA
<213> ORGANISM: artificial
<220> FEATURE:
<223> OTHER INFORMATION: tRNA synthetase based on M. jannaschii tyrosyl-tRNA synthetase

<400> SEQUENCE: 1

```
atggacgaat tgaaatgat  aaagagaaac acatctgaaa ttatcagcga ggaagagtta      60
agagaggttt taaaaaaga  tgaaaaatct gctgggatag gttttgaacc aagtggtaaa     120
atacatttag gcattatct  ccaaataaaa aagatgattg atttacaaaa tgctggattt     180
gatataatta tattgttggc tgatttacac gcctatttaa accagaaagg agagttggat     240
gagattagaa aaataggaga ttataacaaa aaagtttttg aagcaatggg gttaaaggca     300
aaatgtgctt atgaagtcc  tttccagctt gataaggatt atacactgaa tgtctatatga    360
ttggctttaa aaactacctt aaaaagagca agaaggagta tggaacttat agcaagagag     420
gatgaaaatc caaggttgc  tgaagttatc tatccaataa tgcaggttaa tggttatcat     480
tatcttggcg ttgatgttgc agttggaggg atggagcaga aaaaataca  catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
ataatgagaa tagctaaata cttccttgaa tatcctttaa ccataaaaag gccagaaaaa     780
tttggtggag atttgacagt taatagctat gaggagttag agtttattt taaaaataag     840
gaattgcatc caatggattt aaaaaatgct gtagctgaag aacttataaa gattttagag     900
ccaattagaa agagatta                                                   918
```

<210> SEQ ID NO 2
<211> LENGTH: 918
<212> TYPE: DNA
<213> ORGANISM: artificial
<220> FEATURE:
<223> OTHER INFORMATION: tRNA synthetase based on M. jannaschii tyrosyltRNA synthetase

<400> SEQUENCE: 2

| atggacgaat | ttgaaatgat | aaagagaaac | acatctgaaa | ttatcagcga | ggaagagtta | 60 |
| agagaggttt | taaaaaaaga | tgaaaaatct | gctcagatag | gttttgaacc | aagtggtaaa | 120 |
| atacatttag | ggcattatct | ccaaataaaa | aagatgattg | atttacaaaa | tgctggattt | 180 |
| gatataatta | tattgttggc | tgatttacac | gcctatttaa | accagaaagg | agagttggat | 240 |
| gagattagaa | aaataggaga | ttataacaaa | aaagttttg | aagcaatggg | gttaaaggca | 300 |
| aaatatgttt | atggaagtcc | tttccagctt | gataaggatt | atacactgaa | tgtctataga | 360 |
| ttggctttaa | aaactacctt | aaaaagagca | agaaggagta | tggaacttat | agcaagagag | 420 |
| gatgaaaatc | caaggttgc | tgaagttatc | tatccaataa | tgcaggttaa | ttgttctcat | 480 |
| tattatggcg | ttgatgttgc | agttggaggg | atggagcaga | gaaaaataca | catgttagca | 540 |
| agggagcttt | taccaaaaaa | ggttgtttgt | attcacaacc | ctgtcttaac | gggtttggat | 600 |
| ggagaaggaa | agatgagttc | ttcaaaaggg | aattttatag | ctgttgatga | ctctccagaa | 660 |
| gagattaggg | ctaagataaa | gaaagcatac | tgcccagctg | gagttgttga | aggaaatcca | 720 |
| ataatggaga | tagctaaata | cttccttgaa | tatcctttaa | ccataaaaag | gccagaaaaa | 780 |
| tttggtggag | atttgacagt | taatagctat | gaggagttag | agagtttatt | taaaaataag | 840 |
| gaattgcatc | caatggattt | aaaaaatgct | gtagctgaag | aacttataaa | gattttagag | 900 |
| ccaattagaa | agagatta | | | | | 918 |

<210> SEQ ID NO 3
<211> LENGTH: 918
<212> TYPE: DNA
<213> ORGANISM: artificial
<220> FEATURE:
<223> OTHER INFORMATION: tRNA synthetase based on M. jannaschii tyrosyl-
 tRNA synthetase

<400> SEQUENCE: 3

| atggacgaat | ttgaaatgat | aaagagaaac | acatctgaaa | ttatcagcga | ggaagagtta | 60 |
| agagaggttt | taaaaaaaga | tgaaaaatct | gctactatag | gttttgaacc | aagtggtaaa | 120 |
| atacatttag | ggcattatct | ccaaataaaa | aagatgattg | atttacaaaa | tgctggattt | 180 |
| gatataatta | tattgttggc | tgatttacac | gcctatttaa | accagaaagg | agagttggat | 240 |
| gagattagaa | aaataggaga | ttataacaaa | aaagttttg | aagcaatggg | gttaaaggca | 300 |
| aaatatgttt | atggaagtac | gttccagctt | gataaggatt | atacactgaa | tgtctataga | 360 |
| ttggctttaa | aaactacctt | aaaaagagca | agaaggagta | tggaacttat | agcaagagag | 420 |
| gatgaaaatc | caaggttgc | tgaagttatc | tatccaataa | tgcaggttaa | tccgttgcat | 480 |
| tatgctggcg | ttgatgttgc | agttggaggg | atggagcaga | gaaaaataca | catgttagca | 540 |
| agggagcttt | taccaaaaaa | ggttgtttgt | attcacaacc | ctgtcttaac | gggtttggat | 600 |
| ggagaaggaa | agatgagttc | ttcaaaaggg | aattttatag | ctgttgatga | ctctccagaa | 660 |
| gagattaggg | ctaagataaa | gaaagcatac | tgcccagctg | gagttgttga | aggaaatcca | 720 |
| ataatggaga | tagctaaata | cttccttgaa | tatcctttaa | ccataaaaag | gccagaaaaa | 780 |
| tttggtggag | atttgacagt | taatagctat | gaggagttag | agagtttatt | taaaaataag | 840 |
| gaattgcatc | caatggattt | aaaaaatgct | gtagctgaag | aacttataaa | gattttagag | 900 |
| ccaattagaa | agagatta | | | | | 918 |

<210> SEQ ID NO 4
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 4

```
atggacgaat tgaaatgat  aaagagaaac acatctgaaa ttatcagcga ggaagagtta    60
agagaggttt taaaaaaga  tgaaaaatct gctcatatag gttttgaacc aagtggtaaa   120
atacatttag ggcattatct ccaaataaaa aagatgattg atttacaaaa tgctggattt   180
gatataatta tattgttggc tgatttacac gcctatttaa accagaaagg agagttggat   240
gagattagaa aaataggaga ttataacaaa aaagttttg aagcaatggg gttaaaggca   300
aaatatgttt atggaagtga gttccagctt gataaggatt atacactgaa tgtctataga   360
ttggctttaa aaactacctt aaaaagagca agaaggagta tggaacttat agcaagagag   420
gatgaaaatc caaggttgc tgaagttatc tatccaataa tgcaggttaa tcggccgcat   480
tatcctggcg ttgatgttgc agttggaggg atggagcaga gaaaaataca catgttagca   540
agggagcttt taccaaaaaa ggttgtttgt attcacaacc ctgtcttaac gggtttggat   600
ggagaaggaa agatgagttc ttcaaaaggg aattttatag ctgttgatga ctctccagaa   660
gagattaggg ctaagataaa gaaagcatac tgcccagctg gagttgttga aggaaatcca   720
ataatgagga tagctaaata cttccttgaa tatcctttaa ccataaaaag gccagaaaaa   780
tttggtggag atttgacagt taatagctat gaggagttag agagtttatt aaaaataag    840
gaattgcatc caatggattt aaaaaatgct gtagctgaag aacttataaa gattttagag   900
ccaattagaa agagatta                                                918
```

<210> SEQ ID NO 5
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 5

```
atggacgaat tgaaatgat  aaagagaaac acatctgaaa ttatcagcga ggaagagtta    60
agagaggttt taaaaaaga  tgaaaaatct gcttatatag gttttgaacc aagtggtaaa   120
atacatttag ggcattatct ccaaataaaa aagatgattg atttacaaaa tgctggattt   180
gatataatta tattgttggc tgatttacac gcctatttaa accagaaagg agagttggat   240
gagattagaa aaataggaga ttataacaaa aaagttttg aagcaatggg gttaaaggca   300
aaatatgttt atggaagtcc tttccagctt gataaggatt atacactgaa tgtctataga   360
ttggctttaa aaactacctt aaaaagagca agaaggagta tggaacttat agcaagagag   420
gatgaaaatc caaggttgc tgaagttatc tatccaataa tgcaggttaa tcagagtcat   480
tatgatggcg ttgatgttgc agttggaggg atggagcaga gaaaaataca catgttagca   540
agggagcttt taccaaaaaa ggttgtttgt attcacaacc ctgtcttaac gggtttggat   600
ggagaaggaa agatgagttc ttcaaaaggg aattttatag ctgttgatga ctctccagaa   660
gagattaggg ctaagataaa gaaagcatac tgcccagctg gagttgttga aggaaatcca   720
ataatgagga tagctaaata cttccttgaa tatcctttaa ccataaaaag gccagaaaaa   780
tttggtggag atttgacagt taatagctat gaggagttag agagtttatt aaaaataag    840
```

```
gaattgcatc caatggattt aaaaaatgct gtagctgaag aacttataaa gattttagag    900
ccaattagaa agagatta                                                  918

<210> SEQ ID NO 6
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 6
atggacgaat tgaaatgat aaagagaaac acatctgaaa ttatcagcga ggaagagtta     60
agagaggttt taaaaaaga tgaaaaatct gcttcgatag gttttgaacc aagtggtaaa    120
atacatttag gcattatct ccaaataaaa aagatgattg atttacaaaa tgctggattt    180
gatataatta tattgttggc tgatttacac gcctatttaa accagaaagg agagttggat    240
gagattagaa aataggaga ttataacaaa aaagttttg aagcaatggg gttaaaggca     300
aaatatgttt atgaagtac gttccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tacgtatcat    480
tatgctggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918

<210> SEQ ID NO 7
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 7
atggacgaat tgaaatgat aaagagaaac acatctgaaa ttatcagcga ggaagagtta     60
agagaggttt taaaaaaga tgaaaaatct gctcctatag gttttgaacc aagtggtaaa    120
atacatttag gcattatct ccaaataaaa aagatgattg atttacaaaa tgctggattt    180
gatataatta tattgttggc tgatttacac gcctatttaa accagaaagg agagttggat    240
gagattagaa aataggaga ttataacaaa aaagttttg aagcaatggg gttaaaggca     300
aaatatgttt atgaagtat gttccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa taatacgcat    480
tatgggggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
```

```
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918

<210> SEQ ID NO 8
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 8
atggacgaat tgaaatgat  aaagagaaac acatctgaaa ttatcagcga ggaagagtta     60
agagaggttt taaaaaaga  tgaaaaatct gctacgatag gttttgaacc aagtggtaaa    120
atacatttag gcattatct  ccaaataaaa aagatgattg atttacaaaa tgctggattt    180
gatataatta tattgttggc tgatttacac gcctatttaa accagaaagg agagttggat    240
gagattagaa aataggaga  ttataacaaa aaagttttg  aagcaatggg gttaaaggca    300
aaatatgttt atggaagtca tttccagctt gataaggatt atacactgaa tgtctataga    360
ttggctttaa aaactacctt aaaaagagca agaaggagta tggaacttat agcaagagag    420
gatgaaaatc caaggttgc  tgaagttatc tatccaataa tgcaggttaa tcagactcat    480
tatgagggcg ttgatgttgc agttggaggg atggagcaga gaaaaataca catgttagca    540
agggagcttt taccaaaaaa ggttgtttgt attcacaacc ctgtcttaac gggttggat     600 ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918

<210> SEQ ID NO 9
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 9
atggacgaat tgaaatgat  aaagagaaac acatctgaaa ttatcagcga ggaagagtta     60
agagaggttt taaaaaaga  tgaaaaatct gctcatatag gttttgaacc aagtggtaaa    120
atacatttag gcattatct  ccaaataaaa aagatgattg atttacaaaa tgctggattt    180
gatataatta tattgttggc tgatttacac gcctatttaa accagaaagg agagttggat    240
gagattagaa aataggaga  ttataacaaa aaagttttg  aagcaatggg gttaaaggca    300
aaatatgttt atggaagtaa gttccagctt gataaggatt atacactgaa tgtctataga    360
ttggctttaa aaactacctt aaaaagagca agaaggagta tggaacttat agcaagagag    420
gatgaaaatc caaggttgc  tgaagttatc tatccaataa tgcaggttaa tccgtgtcat    480
```

```
tatcatggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaaaggg aatttatag ctgttgatga ctctccagaa       660
gagattaggg ctaagataaa gaaagcatac tgcccagctg gagttgttga aggaaatcca     720
ataatggaga tagctaaata cttccttgaa tatcctttaa ccataaaaag gccagaaaaa     780
tttggtggag atttgacagt taatagctat gaggagttag agagtttatt taaaaataag     840
gaattgcatc caatggattt aaaaaatgct gtagctgaag aacttataaa gattttagag     900
ccaattagaa agagatta                                                   918

<210> SEQ ID NO 10
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 10
atggacgaat ttgaaatgat aaagagaaac acatctgaaa ttatcagcga ggaagagtta      60
agagaggttt taaaaaaaga tgaaaaatct gctgctatag gttttgaacc aagtggtaaa     120
atacatttag ggcattatct ccaaataaaa aagatgattg atttacaaaa tgctggattt     180
gatataatta tattgttggc tgatttacac gcctatttaa accagaaagg agagttggat    240
gagattagaa aataggaga ttataacaaa aaagtttttg aagcaatggg gttaaaggca     300
aaatatgttt atggaagtcg gttccagctt gataaggatt atacactgaa tgtctctata    360
ttggctttaa aaactacctt aaaaagagca agaaggagta tggaacttat agcaagagag    420
gatgaaaatc caaggttgc tgaagttatc tatccaataa tgcaggttaa tgtgattcat     480
tatgatggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aatttatag ctgttgatga ctctccagaa      660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918

<210> SEQ ID NO 11
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 11
atggacgaat ttgaaatgat aaagagaaac acatctgaaa ttatcagcga ggaagagtta     60
agagaggttt taaaaaaaga tgaaaaatct gctgggatag gttttgaacc aagtggtaaa   120
atacatttag ggcattatct ccaaataaaa aagatgattg atttacaaaa tgctggattt   180
gatataatta tattgttggc tgatttacac gcctatttaa accagaaagg agagttggat    240
gagattagaa aataggaga ttataacaaa aaagtttttg aagcaatggg gttaaaggca    300
```

-continued

| | |
|---|---|
| aaatatgttt atgaagtac tttccagctt gataaggatt atacactgaa tgtctataga | 360 |
| ttggctttaa aaactacctt aaaaagagca agaaggagta tggaacttat agcaagagag | 420 |
| gatgaaaatc caaaggttgc tgaagttatc tatccaataa tgcaggttaa tacgtattat | 480 |
| tatgctggcg ttgatgttgc agttggaggg atggagcaga gaaaaataca catgttagca | 540 |
| agggagcttt taccaaaaaa ggttgtttgt attcacaacc ctgtcttaac gggtttggat | 600 |
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagatta | 918 |

<210> SEQ ID NO 12
<211> LENGTH: 918
<212> TYPE: DNA
<213> ORGANISM: artificial
<220> FEATURE:
<223> OTHER INFORMATION: tRNA synthetase based on M. jannaschii tyrosyl-
 tRNA synthetase

<400> SEQUENCE: 12

| | |
|---|---|
| atggacgaat tgaaatgat aaagagaaac acatctgaaa ttatcagcga ggaagagtta | 60 |
| agagaggttt taaaaaaga tgaaaaatct gctctgatag gttttgaacc aagtggtaaa | 120 |
| atacatttag ggcattatct ccaaataaaa aagatgattg atttacaaaa tgctggatt | 180 |
| gatataatta tattgttggc tgatttacac gcctatttaa accagaaagg agagttggat | 240 |
| gagattagaa aaataggaga ttataacaaa aaagttttg aagcaatggg gttaaaggca | 300 |
| aaatatgttt atggaagtcc gttccagctt gataaggatt atacactgaa tgtctataga | 360 |
| ttggctttaa aaactacctt aaaaagagca agaaggagta tggaacttat agcaagagag | 420 |
| gatgaaaatc caaaggttgc tgaagttatc tatccaataa tgcaggttaa tcagattcat | 480 |
| tctagtggcg ttgatgttgc agttggaggg atggagcaga gaaaaataca catgttagca | 540 |
| agggagcttt taccaaaaaa ggttgtttgt attcacaacc ctgtcttaac gggtttggat | 600 |
| ggagaaggaa agatgagttc ttcaaaaggg aatttttatag ctgttgatga ctctccagaa | 660 |
| gagattaggg ctaagataaa gaaagcatac tgcccagctg gagttgttga aggaaatcca | 720 |
| ataatggaga tagctaaata cttccttgaa tatcctttaa ccataaaaag gccagaaaaa | 780 |
| tttggtggag atttgacagt taatagctat gaggagttag agagtttatt taaaaataag | 840 |
| gaattgcatc caatggattt aaaaaatgct gtagctgaag aacttataaa gattttagag | 900 |
| ccaattagaa agagatta | 918 |

<210> SEQ ID NO 13
<211> LENGTH: 918
<212> TYPE: DNA
<213> ORGANISM: artificial
<220> FEATURE:
<223> OTHER INFORMATION: tRNA synthetase based on M. jannaschii tyrosyl-
 tRNA synthetase

<400> SEQUENCE: 13

| | |
|---|---|
| atggacgaat tgaaatgat aaagagaaac acatctgaaa ttatcagcga ggaagagtta | 60 |
| agagaggttt taaaaaaga tgaaaaatct gctggtatag gttttgaacc aagtggtaaa | 120 |

```
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aaagttttg aagcaatggg gttaaaggca       300
aaatatgttt atggaagttc cttccagctt gataaggatt atacactgaa tgtctataga      360
ttggctttaa aaactacctt aaaaagagca agaaggagta tggaacttat agcaagagag      420
gatgaaaatc caaggttgc tgaagttatc tatccaataa tgcaggttaa tacgagtcat      480
tatctgggcg ttgatgttgc agttggaggg atggagcaga gaaaaataca catgttagca      540
agggagcttt taccaaaaaa ggttgtttgt attcacaacc ctgtcttaac gggtttggat      600
ggagaaggaa agatgagttc ttcaaaaggg aatttttatag ctgttgatga ctctccagaa     660
gagattaggg ctaagataaa gaaagcatac tgcccagctg gagttgttga aggaaatcca     720
ataatggaga tagctaaata cttccttgaa tatccttta ccataaaag gccagaaaaa       780 tttggtggag atttgacagt taatagctat gaggagttag agagttatt taaaaataag      840 gaattgcatc caatggattt aaaaaatgct gtagctgaag aacttataaa gattttagag     900
ccaattagaa agagatta                                                    918

<210> SEQ ID NO 14
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 14
atggacgaat ttgaaatgat aaagagaaac acatctgaaa ttatcagcga ggaagagtta      60
agagaggttt taaaaaaga tgaaaaatct gctacgatag gttttgaacc aagtggtaaa      120
atacatttag ggcattatct ccaaataaaa aagatgattg atttacaaaa tgctggattt      180
gatataatta tattgttggc tgatttacac gcctatttaa accagaaagg agagttggat      240
gagattagaa aaataggaga ttataacaaa aaagttttg aagcaatggg gttaaaggca       300
aaatatgttt atggaagtaa tttccagctt gataaggatt atacactgaa tgtctataga      360
ttggctttaa aaactacctt aaaaagagca agaaggagta tggaacttat agcaagagag      420
gatgaaaatc caaggttgc tgaagttatc tatccaataa tgcaggttaa tccgcttcat      480
tatcagggcg ttgatgttgc agttggaggg atggagcaga gaaaaataca catgttagca      540
agggagcttt taccaaaaaa ggttgttttgt attcacaacc ctgtcttaac gggtttggat     600
ggagaaggaa agatgagttc ttcaaaaggg aatttttatag ctgttgatga ctctccagaa    660
gagattaggg ctaagataaa gaaagcatac tgcccagctg gagttgttga aggaaatcca     720
ataatggaga tagctaaata cttccttgaa tatccttta ccataaaag gccagaaaaa       780 tttggtggag atttgacagt taatagctat gaggagttag agagttatt taaaaataag      840 gaattgcatc caatggattt aaaaaatgct gtagctgaag aacttataaa gattttagag     900
ccaattagaa agagatta                                                    918

<210> SEQ ID NO 15
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase
```

<400> SEQUENCE: 15

```
atggacgaat tgaaatgat aaagagaaac acatctgaaa ttatcagcga ggaagagtta      60
agagaggttt taaaaaaaga tgaaaaatct gctacgatag gttttgaacc aagtggtaaa     120
atacatttag ggcattatct ccaaataaaa aagatgattg atttacaaaa tgctggattt     180
gatataatta tattgttggc tgatttacac gcctatttaa accagaaagg agagttggat     240
gagattagaa aataggaga ttataacaaa aaagttttg aagcaatggg gttaaaggca       300
aaatatgttt atggaagtct gttccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tcctcttcat     480
tatgagggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918
```

<210> SEQ ID NO 16
<211> LENGTH: 918
<212> TYPE: DNA
<213> ORGANISM: artificial
<220> FEATURE:
<223> OTHER INFORMATION: tRNA synthetase based on M. jannaschii tyrosyl-tRNA synthetase

<400> SEQUENCE: 16

```
atggacgaat tgaaatgat aaagagaaac acatctgaaa ttatcagcga ggaagagtta      60
agagaggttt taaaaaaaga tgaaaaatct gctcttatag gttttgaacc aagtggtaaa    120
atacatttag ggcattatct ccaaataaaa aagatgattg atttacaaaa tgctggattt     180
gatataatta tattgttggc tgatttacac gcctatttaa accagaaagg agagttggat    240
gagattagaa aataggaga ttataacaaa aaagttttg aagcaatggg gttaaaggca       300
aaatatgttt atggaagtac tttccagctt gataaggatt atacactgaa tgtctataga   360
ttggctttaa aaactacctt aaaaagagca agaaggagta tggaacttat agcaagagag    420
gatgaaaatc caaggttgc tgaagttatc tatccaataa tgcaggttaa tccggttcat    480
tatcagggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918
```

<210> SEQ ID NO 17

```
<211> LENGTH: 918
<212> TYPE: DNA
<213> ORGANISM: artificial
<220> FEATURE:
<223> OTHER INFORMATION: tRNA synthetase based on M. jannaschii tyrosyl-
      tRNA synthetase

<400> SEQUENCE: 17
atggacgaat tgaaatgat aaagagaaac acatctgaaa ttatcagcga ggaagagtta      60
agagaggttt taaaaaaga tgaaaaatct gctactatag gttttgaacc aagtggtaaa     120
atacatttag gcattatct ccaaataaaa aagatgattg atttacaaaa tgctggattt     180
gatataatta tattgttggc tgatttacac gcctatttaa accagaaagg agagttggat    240
gagattagaa aaataggaga ttataacaaa aagttttg aagcaatggg gttaaaggca      300
aaatatgttt atggaagttc gttccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaata tgcaggttaa tccactgcat      480
tatcagggcg ttgatgttgc agttggaggg atggagcaga gaaaatacac catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918

<210> SEQ ID NO 18
<211> LENGTH: 306
<212> TYPE: PRT
<213> ORGANISM: artificial
<220> FEATURE:
<223> OTHER INFORMATION: tRNA synthetase based on M. jannaschii tyrosyl-
      tRNA synthetase

<400> SEQUENCE: 18

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
```

```
                145                 150                 155                 160
Tyr Arg Gly Val Asp Val Ala Val Gly Gly Met Glu Gln Arg Lys Ile
165                 170                 175

His Met Leu Ala Arg Glu Leu Leu Pro Lys Lys Val Val Cys Ile His
180                 185                 190

Asn Pro Val Leu Thr Gly Leu Asp Gly Glu Gly Lys Met Ser Ser Ser
195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
245                 250                 255

Arg Pro Glu Lys Phe Gly Gly Asp Leu Thr Val Asn Ser Tyr Glu Glu
260                 265                 270

Leu Glu Ser Leu Phe Lys Asn Lys Glu Leu His Pro Met Asp Leu Lys
275                 280                 285

Asn Ala Val Ala Glu Glu Leu Ile Lys Ile Leu Glu Pro Ile Arg Lys
290                 295                 300

Arg Leu
305

<210> SEQ ID NO 19
<211> LENGTH: 306
<212> TYPE: PRT
<213> ORGANISM: artificial
<220> FEATURE:
<223> OTHER INFORMATION: tRNA synthetase based on M. jannaschii tyrosyl-
      tRNA synthetase

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
20                  25                  30

Ile Gly Phe Glu Pro Ser Gly Lys Ile His Leu Gly His Tyr Leu Gln
35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
85                  90                  95

Gly Leu Lys Ala Lys Tyr Val Tyr Gly Ser Glu Phe Gln Leu Asp Lys
100                 105                 110

Asp Tyr Thr Leu Asn Val Tyr Arg Leu Ala Leu Lys Thr Thr Leu Lys
115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
165                 170                 175

His Met Leu Ala Arg Glu Leu Leu Pro Lys Lys Val Val Cys Ile His
180                 185                 190

Asn Pro Val Leu Thr Gly Leu Asp Gly Glu Gly Lys Met Ser Ser Ser
```

```
            195                 200                 205
Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
245                 250                 255

Arg Pro Glu Lys Phe Gly Gly Asp Leu Thr Val Asn Ser Tyr Glu Glu
260                 265                 270

Leu Glu Ser Leu Phe Lys Asn Lys Glu Leu His Pro Met Asp Leu Lys
275                 280                 285

Asn Ala Val Ala Glu Glu Leu Ile Lys Ile Leu Glu Pro Ile Arg Lys
290                 295                 300

Arg Leu
305

<210> SEQ ID NO 20
<211> LENGTH: 306
<212> TYPE: PRT
<213> ORGANISM: artificial
<220> FEATURE:
<223> OTHER INFORMATION: tRNA synthetase based on M. jannaschii tyrosyl-
      tRNA synthetase

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
```

```
245                 250                 255
Arg Pro Glu Lys Phe Gly Gly Asp Leu Thr Val Asn Ser Tyr Glu Glu
260                 265                 270

Leu Glu Ser Leu Phe Lys Asn Lys Glu Leu His Pro Met Asp Leu Lys
275                 280                 285

Asn Ala Val Ala Glu Glu Leu Ile Lys Ile Leu Glu Pro Ile Arg Lys
290                 295                 300

Arg Leu
305

<210> SEQ ID NO 21
<211> LENGTH: 77
<212> TYPE: RNA
<213> ORGANISM: Methanococcus jannaschii

<400> SEQUENCE: 21
ccggcgguag uucagcaggg cagaacggcg gacucuaaau ccgcauggcg cugguucaaa      60
uccggcccgc cggacca                                                    77

<210> SEQ ID NO 22
<211> LENGTH: 10
<212> TYPE: PRT
<213> ORGANISM: Artificial
<220> FEATURE:
<223> OTHER INFORMATION: N-terminal tryptic peptide of Z domain protein
      including p-acetyl-L-phenylalanine
<220> FEATURE:
<221> NAME/KEY: MISC_FEATURE
<222> LOCATION: (7)..(7)
<223> OTHER INFORMATION: X is p-acetyl-L-phenylalanine

<400> SEQUENCE: 22

Met Thr Ser Val Asp Asn Xaa Ile Asn Lys
1               5                   10

<210> SEQ ID NO 23
<211> LENGTH: 38
<212> TYPE: DNA
<213> ORGANISM: Artificial
<220> FEATURE:
<223> OTHER INFORMATION: PCR primer

<400> SEQUENCE: 23
gaggaatccc atatggacga atttgaaatg ataaagag                             38

<210> SEQ ID NO 24
<211> LENGTH: 36
<212> TYPE: DNA
<213> ORGANISM: Artificial
<220> FEATURE:
<223> OTHER INFORMATION: PCR primer

<400> SEQUENCE: 24
cgtttgaaac tgcagttata atctctttct aattgg                               36
```

SITE SPECIFIC INCORPORATION OF KETO AMINO ACIDS INTO PROTEINS

CROSS-REFERENCE TO RELATED APPLICATIONS

This application is a continuation of Ser. No. 10/530,421, filed Apr. 5, 2005, which is a 371 application of international application no. PCT/US2003/032576, filed Oct. 15, 2003, which claims priority to and benefit of U.S. provisional patent application Ser. No. 60/419,265, filed Oct. 16, 2002, and, U.S. provisional patent application Ser. No. 60/420,990, filed Oct. 23, 2002, the specifications of which are incorporated herein in their entirety.

STATEMENT AS TO RIGHTS TO INVENTIONS MADE UNDER FEDERALLY SPONSORED RESEARCH AND DEVELOPMENT

The invention was made with United States Government support under Contract No. NIH GM62159 from the National Institutes of Health; Contract nos. DE-FG03-00ER45812 and DE-AC03-76SF00098 from the Department of Energy; and Contract No. ONR-6502573 by the Office of Naval Research. The United States Government has certain rights in the invention.

FIELD OF THE INVENTION

The invention is in the field of translation biochemistry. The invention relates to methods for producing and compositions of orthogonal tRNAs, orthogonal aminoacyl-tRNA synthetases and pairs thereof that incorporate keto amino acids into proteins. The invention also relates to methods of producing proteins in cells using such pairs and related compositions.

BACKGROUND OF THE INVENTION

The genetic codes of all known organisms encode the same common twenty amino acids as building blocks for the biosynthesis of proteins. The side chains of these amino acids comprise a surprisingly limited number of functional groups—nitrogen bases, carboxylic acids and amides, alcohols, and a thiol group (and in rare cases, selenocysteine (see, e.g., Bock, A., et al., (1991) *Mol. Microbiol.* 5:515-520) or pyrrolysine (see, e.g., Srinivasan, G., et al., (2002) *Science* 296:1459-1462; Hao, B., et al., (2002) *Science* 296:1462-1466)), the remainder being simple alkanes or hydrophobic groups. The ability to augment the genetically encoded amino acids with new amino acids, for example, amino acids with metal chelating, fluorescent, redox active, photoactive or spin-labeled side chains, would significantly enhance the ability to manipulate the structures and functions of proteins and perhaps living organisms themselves. Recently, it was reported that by adding new components to the translational machinery of *Escherichia coli*, one could site-specifically incorporate with high fidelity a number of unnatural amino acids into proteins in vivo. See, e.g., Wang, L., et al., (2001) *Science* 292:498-500; Wang, L., et al., (2002) *J. Am. Chem. Soc.* 124:1836-1837; and, Zhang, Z., et al., (2002) *Angew. Chem. Int. Ed. Engl.* 41:2840-2842.

The keto group is ubiquitous in organic chemistry, and participates in a large number of reactions from addition and decarboxylation reactions to aldol condensations. Moreover, the unique reactivity of the carbonyl group allows it to be selectively modified with hydrazide and hydroxylamine derivatives in the presence of the other amino acid side chains. See, e.g., Cornish, V. W., et al., (1996) *J. Am. Chem. Soc.* 118:8150-8151; Geoghegan, K. F. & Stroh, J. G. (1992) *Bioconjug. Chem.* 3:138-146; and, Mahal, L. K., et al., (1997) *Science* 276:1125-1128. Although present in cofactors (see, e.g., Begley, T. P., et al., (1997) in *Top. Curr. Chem.*, eds. Leeper, F. J. & Vederas, J. C. (Springer-Verlag, New York), Vol. 195, pp. 93-142), metabolites (see, e.g., Diaz, E., et al., (2001) *Microbiol. Mol. Biol. Rev.* 65:523-569), and as a posttranslational modification to proteins (see, e.g., Okeley, N. M. & van der Donk, W. A. (2000) *Chem. Biol.* 7, R159-R171), this important functional group is absent from the side chains of the common amino acids. The addition of the carbonyl side chain to an amino acid would allow proteins comprising this amino acid to participate in a large number of reactions from addition and decarboxylation reactions to aldol condensations, e.g., to be selectively modified with hydrazide and hydroxylamine derivatives.

The keto group provides a unique chemical reactivity not present in the common twenty amino acids due to its ability to participate in addition reactions involving either the carbonyl group or the acidic Cα position. This group also provides an alternative to the natural amino acid cysteine for the selective modification of proteins with a large variety of chemical reagents. The reactive thiol group of cysteine has been extensively used to attach various biophysical probes to proteins. See, e.g., Creighton, T. E. (1986) *Methods Enzymol.* 131:83-106; Altenbach, C., et al., (1990) *Science* 248:1088-92; Brinkley, M. (1992) *Bioconjug. Chem.* 3:2-13; Giuliano, K. A., et al., (1995) *Annu. Rev. Biophys. Biomol. Struct.* 24:405-34; Mannuzzu, L. M., et al., (1996) *Science* 271:213-6; Griffin, B. et al., (1998) *Science* 281:269-272; Wu et al., (2000) *Methods Enzymol.* 327:546-64; and, Gaietta, G., et al., (2002) *Science* 296:503-7. Unfortunately, the labeling of single cysteine residues is often complicated by the presence of more than one accessible cysteine residue in a protein, as well as exchange reactions of the resulting disulfide in the presence of free thiol. Therefore, the availability of a nonproteinogenic amino acid with orthogonal reactivity makes possible selective modification of protein in cases where a single cysteine cannot be selectively labeled, where two different labels are needed, and where a disulfide linkage may not be sufficiently stable. The carbonyl group reacts readily with hydrazides, hydroxylamines, and semicarbazides under mild conditions in aqueous solution, and forms hydrazone, oxime, and semicarbazone linkages, respectively, which are stable under physiological conditions. See, e.g., Jencks, W. P. (1959) *J. Am. Chem. Soc.* 81, 475-481; Shao, J. & Tam, J. P. (1995) *J. Am. Chem. Soc.* 117:3893-3899.

Several methods have been developed to selectively incorporate the carbonyl group into peptides and proteins. Initially, an aldehyde was introduced at the N-termini of peptides by oxidizing N-terminal serine or threonine with periodate, followed by coupling to biotin and fluorescent reporters through a hydrazone linkage. See, e.g., Geoghegan, K. F. & Stroh, J. G. (1992) *Bioconjug. Chem.* 3:138-146. This method is, however, restricted to the N-terminal modification of proteins. Solid phase peptide synthesis was later employed for the preparation of peptide segments containing either a hydrazide or hydroxylamine, which subsequently react with a branched aldehyde core matrix to form peptide dendrimers (see, e.g., Shao, J. & Tam, J. P. (1995) *J. Am. Chem. Soc.* 117:3893-3899; Rose, K. (1994) *J. Am. Chem. Soc.* 116:30-33), or with a keto containing peptide segment to form synthetic proteins (see, e.g., Canne, L. E., et al., (1995) *J. Am. Chem. Soc.* 117:2998-3007). This approach is generally applicable to peptides or small proteins of less than 100 residues, but is limited by the difficulties associated with the synthesis of large peptides or proteins.

An in vitro biosynthetic method has also been used to incorporate the keto group into proteins. See, e.g., Cornish, V. W., et al., (1996), supra. In this method, the unnatural amino acid containing the keto group is chemically acylated to an amber suppressor tRNA. When the acylated tRNA and the mutant gene are combined in an in vitro extract capable of supporting protein biosynthesis, the unnatural amino acid is selectively incorporated in response to a UAG codon. This method requires the suppressor tRNA to be chemically aminoacylated with the unnatural amino acid in vitro, and the acylated tRNA is consumed as a stoichiometric reagent during translation and cannot be regenerated, resulting in low protein yields.

To further expand the genetic code and increase the diversity of unnatural amino acid structures with, e.g., a keto amino acid, that can be incorporated into proteins in a cell, there is a need to develop improved and/or additional components of the biosynthetic machinery, e.g., orthogonal tRNAs, orthogonal aminoacyl-tRNA synthetases and/or unique codons that can utilize a keto amino acid and that can be regenerated. This invention fulfills these and other needs, as will be apparent upon review of the following disclosure.

SUMMARY OF THE INVENTION

The invention provides compositions and methods of producing orthogonal components for incorporating a keto amino acid into a growing polypeptide chain in response to a selector codon, e.g., stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof, which can be used to incorporate keto amino acids into growing polypeptide chains.

Typically, an orthogonal aminoacyl-tRNA synthetase (O-RS) of the invention preferentially aminoacylates an O-tRNA with an efficiency of at least about, e.g., a 45%, a 50%, a 60%, a 75%, a 80%, or a 90% or more the efficiency of a polypeptide comprising an amino acid sequence of SEQ ID NO.: 18 with a keto amino acid. In certain embodiments, the O-RS comprises an amino acid sequence comprising any one of SEQ ID NO.: 18-20, or a conservative variation thereof.

A composition that includes an O-RS can optionally further includes an orthogonal tRNA (O-tRNA), where the O-tRNA recognizes a selector codon. In certain embodiments, the O-tRNA comprises or is encoded by a polynucleotide sequence of SEQ ID NO.:21. A composition that includes an O-RS can optionally includes a cell (e.g., a non-eukaryotic cell, such as an E. coli cell and the like, or a eukaryotic cell), and/or a translation system.

A cell (e.g., a non-eukaryotic cell, or a eukaryotic cell) comprising a translation system is also provided by the invention, where the translation system includes an orthogonal tRNA (O-tRNA); an orthogonal aminoacyl-tRNA synthetase (O-RS); and a keto amino acid. Typically, the O-RS preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with the first keto amino acid. The O-tRNA recognizes the first selector codon, and the O-RS preferentially aminoacylates the O-tRNA with a keto amino acid, e.g., a p-acetyl-L-phenylalanine. In certain embodiments, the O-tRNA comprises or is encoded by a polynucleotide sequence as set forth in SEQ ID NO.: 21, or a complementary polynucleotide sequence thereof. In certain embodiments, the O-RS comprises an amino acid sequence as set forth in any one of SEQ ID NO.: 18-20, or a conservative variation thereof. Optionally, a cell of the invention includes a nucleic acid that comprises a polynucleotide that encodes a polypeptide of interest, where the polynucleotide comprises a selector codon that is recognized by the O-tRNA.

A cell of the invention optionally includes an E. coli cell that includes an orthogonal-tRNA (O-tRNA), an orthogonal aminoacyl-tRNA synthetase (O-RS), a keto amino acid, and a nucleic acid that comprises a polynucleotide that encodes a polypeptide of interest, where the polynucleotide comprises the selector codon that is recognized by the O-tRNA. Typically, the O-RS preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid.

In certain embodiments of the invention, an O-tRNA of the invention comprises or is encoded by a polynucleotide sequence as set forth in SEQ ID NO.: 21, or a complementary polynucleotide sequence thereof. In certain embodiments of the invention, an O-RS comprises an amino acid sequence as set forth in SEQ ID NO.: 18-20, or a conservative variation thereof.

The O-tRNA and/or the O-RS of the invention can be derived from any of a variety of organisms (e.g., eukaryotic and/or non-eukaryotic organisms). In certain embodiments, the O-RS and the O-tRNA are derived from a *Methonococcus jannaschii*.

Polypeptides and polynucleotides are also a feature of the invention. A polypeptide of the invention includes an artificial (e.g., man-made, and not naturally occurring) polypeptide comprising an amino acid as set forth in SEQ ID NO.: 18-20, and/or conservative variations. A polynucleotide of the invention includes an artificial polynucleotide that encodes a polypeptide comprising an amino acid as set forth in SEQ ID NO.: 18-20.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing a protein in a cell (e.g., a non-eukaryotic cell, such as an E. coli cell or the like, or a eukaryotic cell) with a keto amino acid at a specified position are also a feature of the invention. For example, a method includes growing, in an appropriate medium, a cell, where the cell comprises a nucleic acid that comprises at least one selector codon and encodes a protein, providing the keto amino acid, and incorporating the keto amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid (e.g., a p-acetyl-L-phenylalanine). In certain embodiments, the O-RS comprises an amino acid sequence that comprises any one of SEQ ID NO.: 18-20. In certain embodiments, the O-tRNA comprises or is encoded by a polynucleotide sequence as set forth in SEQ ID NO.: 21, or a complementary polynucleotide sequence thereof.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or other translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functional endogenous complementary molecule in the cell. For example, an orthogonal tRNA in a translation system of interest is aminoacylated by any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS.

Cognate: The term "cognate" refers to components that function together, e.g., an orthogonal tRNA and an orthogonal aminoacyl-tRNA synthetase. The components can also be referred to as being complementary.

Preferentially aminoacylates: The term "preferentially aminoacylates" refers to an efficiency, e.g., 70% efficiency, 75% efficiency, 85% efficiency, 90% efficiency, 95% efficiency, or 99% or more efficiency, at which an O-RS aminoacylates an O-tRNA with a keto amino acid as compared to the O-RS aminoacylating a naturally occurring tRNA or a starting material used to generate the O-tRNA.

Selector codon: The term "selector codon" refers to codons recognized by the O-tRNA in the translation process and not typically recognized by an endogenous tRNA. The O-tRNA anticodon loop recognizes the selector codon on the mRNA and incorporates its amino acid, e.g., an unnatural amino acid, such as a keto amino acid, at this site in the polypeptide. Selector codons can include, e.g., nonsense codons, such as stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, and/or the like.

Suppression activity: The term "suppression activity" refers to the ability of a tRNA, e.g., a suppressor tRNA, to read through a selector codon.

Translation system: The term "translation system" refers to the components necessary to incorporate a naturally occurring amino acid into a growing polypeptide chain (protein). Components of a translation system can include, e.g., ribosomes, tRNAs, synthetases, mRNA and the like. The components of the invention can be added to an in vitro or in vivo translation system, e.g., a non-eukaryotic cell, e.g., a bacterium (such as *E coli*), an Archael, or a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, such as a keto amino acid, that is not one of the 20 common naturally occurring amino acids or seleno cysteine or pyrrolysine.

Derived from: As used herein, the term "derived from" refers to a component that is isolated from or made using information from a specified molecule or organism.

Positive selection or screening marker: As used herein, the term "positive selection or screening marker" refers to a marker that when present, e.g., expressed, activated or the like, results in identification of a cell, which comprise the trait, e.g., cells with the positive selection marker, from those without the trait.

Negative selection or screening marker: As used herein, the term "negative selection or screening marker" refers to a marker that when present, e.g., expressed, activated or the like, allows identification of a cell that does not comprise the property or trait (e.g., as compared to a cell that does possess the property or trait).

Reporter: As used herein, the term "reporter" refers to a component that can be used to select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), Adh (alcohol dehydrogenase), his3, ura3, leu2, lys2, or the like.

Eukaryote: As used herein, the term "eukaryote" refers to organisms belonging to the phylogenetic domain Eucarya such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g., *Methanococcus jannaschii* (Mj), *Methanosarcina mazei* (Mm), *Methanobacterium thermoautotrophicum* (Mt), *Methanococcus maripaludis, Methanopyrus kandleri, Halo-* bacterium such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum, Thermoplasma volcanium*, etc.) phylogenetic domain.

Conservative variant: The term "conservative variant" refers to a translation component, e.g., a conservative variant O-tRNA or a conservative variant O-RS, that functionally performs like the component from which the conservative variant is based, e.g., an O-tRNA or O-RS, but having variations in the sequence. For example, an O-RS will aminoacylate a complementary O-tRNA or a conservative variant O-tRNA with an unnatural amino acid, e.g., a keto amino acid, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for a selection/screening of certain components from a population. For example, a selection or screening agent includes, but is not limited to, e.g., a nutrient, an antibiotic, a wavelength of light, an antibody, an expressed polynucleotide, or the like. The selection agent can be varied, e.g., by concentration, intensity, etc.

In response to: As used herein, in the context of translation with O-tRNA and O-RS components, the term "in response to" refers to the process in which a tRNA of the invention recognizes a selector codon and mediates the incorporation of a keto amino acid, which is bound to tRNA, into the growing polypeptide chain.

DETAILED DESCRIPTION

Figure 1:
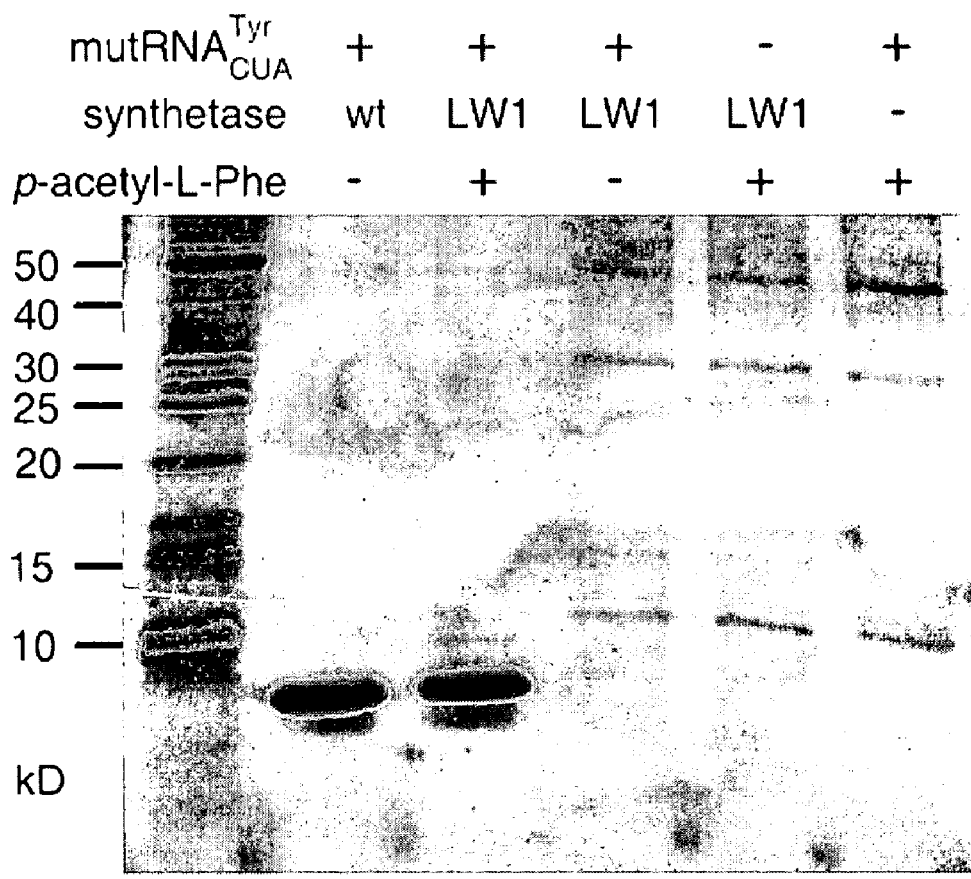
FIG. 1 illustrates a SDS-PAGE analysis of Z domain accumulated under different expression conditions. The left lane is a molecular weight marker.

Although the carbonyl group is the most versatile of the functional groups in organic chemistry, it is absent in the genetically encoded amino acids. To overcome this natural limitation on protein biosynthesis, an orthogonal tRNA-synthetase pair is needed that makes possible the in vivo incorporation of a keto amino acid into proteins in *E. coli* with high translational fidelity in response to the amber nonsense codon. One advantage of this amino acid is that a protein can be selectively modified in vitro or in vivo with, e.g., any one of a variety of molecules, such as a small molecule fluorophore, biotin derivative, etc. This new genetically encoded amino acid expands the ability to manipulate protein structure and function both in vitro and in living cells.

In order to add additional synthetic amino acids, such as a keto amino acid, to the genetic code, in vivo, new orthogonal pairs of an aminoacyl-tRNA synthetase and a tRNA are needed that can function efficiently in the translational machinery, but that is "orthogonal" meaning that it functions independently of the synthetases and tRNAs endogenous to the host cell. Desired characteristics of the pair include a tRNA that decodes or recognizes only a specific new codon, e.g., a selector codon, that is not decoded by any endogenous tRNA, and an aminoacyl-tRNA synthetase that preferentially aminoacylates (or charges) its tRNA with only a specific keto amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., which there are 21 in *E. coli*.

This invention provides compositions of and methods for identifying and producing additional orthogonal tRNA-aminoacyl-tRNA synthetase pairs, e.g., O-tRNA/O-RS pairs that can be used to incorporate a keto amino acid. An O-tRNA of the invention is capable of mediating incorporation of a keto amino acid into a protein that is encoded by a polynucleotide, which comprises a selector codon that is recognized by the O-tRNA, e.g., in vivo. The anticodon loop of the O-tRNA recognizes the selector codon on an mRNA and incorporates its amino acid, e.g., a keto amino acid at this site in the polypeptide. An orthogonal aminoacyl-tRNA synthetase of the invention preferentially aminoacylates (or charges) its O-tRNA with only a specific keto amino acid.

Orthogonal tRNA/Orthogonal Aminoacyl-tRNA Synthetases and Pairs Thereof

Translation systems that are suitable for making proteins that include one or more unnatural amino acids, e.g., keto amino acids, are described in International patent applications WO 2002/086075, entitled "METHODS AND COMPOSITION FOR THE PRODUCTION OF ORTHOGONAL tRNA-AMINOACYLtRNA SYNTHETASE PAIRS" and WO 2002/085923, entitled "IN VIVO INCORPORATION OF UNNATURAL AMINO ACIDS." This application is incorporated herein by reference in its entirety. Such translation systems generally comprise cells (e.g., non-eukaryotic cells, or eukaryotic cells) that include an orthogonal tRNA (O-tRNA), an orthogonal aminoacyl tRNA synthetase (O-RS), and a keto amino acid, where the an orthogonal aminoacyl-tRNA synthetase (O-RS) preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid. An orthogonal pair of the invention includes of an O-tRNA, e.g., a suppressor tRNA, a frameshift tRNA, or the like, and an O-RS. Individual components are also provided in the invention.

The O-RS aminoacylates the O-tRNA with the keto amino acid with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid. The cell uses the components to incorporate the keto amino acid into a growing polypeptide chain, e.g., via a nucleic acid that comprises a polynucleotide that encodes a polypeptide of interest, where the polynucleotide comprises a selector codon that is recognized by the O-tRNA. In certain embodiments of the invention, a cell includes an *E. coli* cell that includes an orthogonal tRNA (O-tRNA), an orthogonal aminoacyl-tRNA synthetase (O-RS), a keto amino acid; and, a nucleic acid that comprises a polynucleotide that encodes a polypeptide of interest, where the polynucleotide comprises the selector codon that is recognized by the O-tRNA and where O-RS preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid. The translation system can also be an in vitro system.

The O-tRNA and/or the O-RS can be naturally occurring or can be derived by mutation of a naturally occurring tRNA and/or RS, e.g., which generates libraries of tRNAs and/or libraries of RSs, from a variety of organisms. For example, one strategy of producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases, that is the host cell synthetases do not aminoacylate the heterologous tRNA.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention mediates incorporation of a keto amino acid into a protein that is encoded by a polynucleotide that comprises a selector codon that is recognized by the O-tRNA, e.g., in vivo or in vitro.

An example of an O-tRNA of the invention is SEQ ID NO.: 21. See Table 2 and Example 3, herein, for sequences of exemplary O-tRNA and O-RS molecules. See also the section entitled "Nucleic Acid and Polypeptide Sequence and Variants" herein. In the tRNA molecule, Thymine (T) is replace with Uracil (U). Additional modifications to the bases can also be present. The invention also includes conservative variations of O-tRNA. For example, conservative variations of O-tRNA include those molecules that function like the O-tRNA of SEQ ID NO.: 21 and maintain the tRNA L-shaped structure, but do not have the same sequence (and are other than wild type tRNA molecules). See also the section herein entitled "Nucleic acids and Polypeptides Sequence and Variants."

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TψC arm or loop, other regions of the tRNA molecule, or a combination thereof. Typically, mutations in a tRNA include mutating the anticodon loop of each member of the library of mutant tRNAs to allow recognition of a selector codon. The method can further include adding an additional sequence (CCA) to 3' terminus of the O-tRNA. Typically, an O-tRNA possesses an improvement of orthogonality for a desired organism compared to the starting material, e.g., the plurality of tRNA sequences, while preserving its affinity towards a desired RS.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at position a certain position, are constructed. Cells, e.g., bacteria, are transformed with these polynucleotides. In the case of an orthogonal tRNA, which cannot be efficiently charged by endogenous E. coli synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNAs, or tRNAs that cannot efficiently be recognized by the synthetase of interest. The cell harboring the non-functional or tRNAs that are not efficiently recognized by the synthetase of interest are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin). In one aspect of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that utilized a keto amino acid. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. See Example 4 herein. Optionally, the marker includes an affinity based screening marker. See Francisco, J. A., et al., (1993) *Production and fluorescence-activated cell sorting of Escherichia coli expressing a functional antibody fragment on the external surface. Proc Natl Acad Sci USA*. 90:10444-8.

Additional methods for producing a recombinant orthogonal tRNA can be found, e.g., in International patent applications WO 2002/086075, supra. See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100 (10): 5676-5681.

Orthogonal aminoacyl-tRNA Synthetase (O-RS)

An O-RS of the invention preferentially aminoacylates an O-tRNA with a keto amino acid in vitro or in vivo. Typically, an O-RS of the invention preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid. A composition comprising an O-RS can further include an orthogonal tRNA (O-tRNA), where the O-tRNA recognizes a selector codon and mediates the incorporation of the keto amino acid. In certain embodiments, a composition including an O-RS can further include a translation system (e.g., in vitro or in vivo). An O-RS of the invention can be provided to the translation system, e.g., a cell, by a polypeptide that includes an O-RS and/or by a polynucleotide that encodes an O-RS or a portion thereof. For example, an O-RS that aminoacylates an O-tRNA with a keto amino acid comprises an amino acid sequence as set forth in any one of SEQ ID NO.: 18-20, or a conservative variation thereof. In another example, an O-RS, or a portion thereof, is encoded by a polynucleotide sequence that encodes an amino acid comprising any one of SEQ ID NO.: 18-20, or a complementary polynucleotide sequence thereof. Additional components for other unnatural amino acids include, e.g., an O-RS, or a portion thereof, that is encoded by a polynucleotide sequence, e.g., of SEQ ID NOs: 1-17. See, e.g., Table 2 and Example 3 herein for sequences of exemplary O-RS molecules. See also the section entitled "Nucleic Acid and Polypeptide Sequence and Variants" herein.

A nucleic acid that comprises a polynucleotide that encodes a polypeptide of interest, where the polynucleotide comprises a selector codon that is recognized by the O-tRNA, or a combination of one or more of these can also be present in the cell. See also the section herein entitled "Orthogonal tRNA."

Methods for identifying an orthogonal aminoacyl-tRNA synthetase (O-RS), e.g., an O-RS, for use with an O-tRNA, are also a feature of the invention. An O-RS can be manipulated to alter the substrate specificity of the synthetase so that only a desired unnatural amino acid, e.g., a keto amino acid, but not any of the common 20 amino acids are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., the keto amino acid. In one aspect of the invention, the steps are performed multiple times, e.g., at least two times.

Additional levels of selection/screening stringency can also be used in the methods of the invention for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional details for producing O-RS, for altering the substrate specificity of the synthetase, for other examples of O-RSs can be found in WO 2002/086075, supra. See also, Example 4, herein, for selecting/screening for altered substrate specificity of an O-RS with a FACS based system.

Source and Host Organisms

The translational components of the invention are typically derived from non-eukaryotic organisms. For example, the orthogonal O-tRNA can be derived from a non-eukaryotic organism (or a combination of organisms), e.g., an archaebacterium, such as *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum pernix*, *Methanococcus maripaludis*, *Methanopyrus kandleri*, *Methanosarcina mazei* (Mm), *Pyrobaculum aerophilum*, *Pyrococcus abyssi*, *Sulfolobus solfataricus* (Ss), *Sulfolobus tokodaii*, *Thermoplasma acidophilum*, *Thermoplasma volcanium*, or the like, or a eubacterium, such as *Escherichia coli*, *Thermus thermophilus*, *Bacillus stearothermphilus*, or the like, while the orthogonal O-RS can be derived from a non-eukaryotic organism (or a combination of organisms), e.g., an archaebacterium, such as *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum pernix*, *Methanococcus maripaludis*, *Methanopyrus kandleri*, *Methanosarcina mazei*, *Pyrobaculum aerophilum*, *Pyrococcus abyssi*, *Sulfolobus solfataricus*, *Sulfolobus tokodaii*, *Thermoplasma acidophilum*, *Thermoplasma volcanium*, or the like, or a eubacterium, such as *Escherichia coli*, *Thermus thermophilus*, *Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and/or O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a non-eukaryotic cells, or eukaryotic cells, to produce a polypeptide with a keto amino acid. A non-eukaryotic cell can be from a variety of sources, e.g., a eubacterium, such as *Escherichia coli*, *Thermus thermophilus*, *Bacillus stearothermphilus*, or the like, or an archaebacterium, such as *Methanococcus jannaschii*, *Methanobacterium thermoautotrophicum*, *Halobacterium* such as *Haloferax volcanii* and *Halobacterium* species NRC-1, *Archaeoglobus fulgidus*, *Pyrococcus furiosus*, *Pyrococcus horikoshii*, *Aeuropyrum*

*pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like. A eukaryotic cell can be from a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of cells with translational components of the invention are also a feature of the invention.

Selector Codons

Selector codons of the invention expand the genetic codon framework of protein biosynthetic machinery to incorporate a keto amino acid. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous incorporation of multiple unnatural amino acids, e.g., keto amino acids and other unnatural amino acids, using these different selector codons.

In one embodiment, the methods involve the use of a selector codon that is a stop codon for the incorporation of a keto amino acid in vivo in a cell. For example, an O-tRNA is produced that recognizes the stop codon and is aminoacylated by an O-RS with a keto amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3'*Exonuclease in phosphorothioate-based oligonucleotide-directed mutagenesis. Nucleic Acids Res,* 791-802. When the O-RS, O-tRNA and the nucleic acid that encodes a polypeptide of interest are combined, e.g., in vivo, the keto amino acid is incorporated in response to the stop codon to give a polypeptide containing the keto amino acid at the specified position. In one embodiment of the invention, a stop codon used as a selector codon is an amber codon, UAG, and/or an opal codon, UGA. In one example, a genetic code in which UAG and UGA are both used as selector codons can encode 22 amino acids while preserving the ochre nonsense codon, UAA, which is the most abundant native termination signal in, e.g., *E. coli.*

The incorporation of keto amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA.

Keto amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNAArg, which exists as a minor species in *Escherichia coli.* In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.,* 25:4685 (1997). Components of the invention can be generated to use these rare codons in vivo.

Selector codons also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids such as a keto amino acid, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pairs. See Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate a keto amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

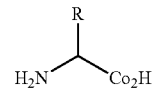

An unnatural amino acid is typically any structure having Formula I, wherein the R group is any substituent other than one used in the twenty natural amino acids. See, e.g., *Biochemistry* by L. Stryer, $3^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention optionally differ from the natural amino acids in side chain, the unnatural amino acids can typically form amide bonds with other amino acids, e.g., natural or unnatural, in the same manner in which they are formed in naturally occurring proteins. However, the unnatural amino acids have side chain groups that distinguish them from the natural amino acids.

Of particular interest in incorporating unnatural amino acids into proteins is to have the ability to incorporate a keto amino acid. The keto group provides a unique chemical reactivity not present in the common twenty amino acids due to its ability to participate in addition reactions involving either the carbonyl group or the acidic Cα position. The carbonyl group reacts readily with, e.g., hydrazides, hydroxylamines, semicarbazides, etc. under mild conditions in aqueous solution, and forms, e.g., hydrazone, oxime, and semicarbazone linkages, respectively, which are stable under physiological conditions. See, e.g., Jencks, W. P. (1959) *J. Am. Chem. Soc.* 81, 475-481; Shao, J. & Tam, J. P. (1995) *J. Am. Chem. Soc.* 117:3893-3899. Through the keto amino acid, proteins can be selectively labeled with a wide variety of other hydrazide or hydroxylamine derivatives (including sugars, fluorescence labels, biotin derivatives, spin labels, metal chelators, crosslinking agents, polyethers, fatty acids, toxins, etc.). See, e.g., the addition of saccharide derivatives through a keto amino acid, e.g., in the application entitled "Glycoprotein synthesis," Ser. No. 10/686,944 filed on Oct. 15, 2003, which is incorporated by reference.

For additional other unnatural amino acids, for example, R in Formula I optionally comprises an alkyl-, aryl-, acyl-, azido-, hydroxyl-, hydrazine, cyano-, halo-, hydrazide, alkenyl, alkynyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Glutamine analogs of the invention include, but are not limited to, α-hydroxy derivatives, γ-substituted derivatives, cyclic derivatives, and amide substituted glutamine derivatives. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, glycosylated amino acids, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety. In some embodiments, the unnatural amino acids have a photoactivatable cross-linker.

In addition to unnatural amino acids that contain novel side chains, unnatural amino acids also optionally comprise modified backbone structures, e.g., as illustrated by the structures of Formula II and III:

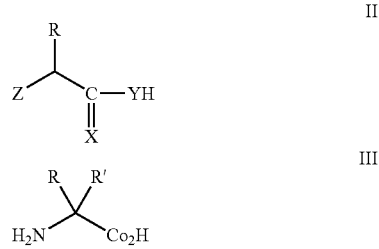

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

In certain embodiments of the invention, a keto amino acid is a derivative of a tyrosine or phenyalanine amino acid. Many unnatural amino acids (such as keto amino acids) are based on natural amino acids, such as tyrosine, phenylalanine, and the like. Tyrosine analogs include para-substituted tyrosines, ortho-substituted tyrosines, and meta substituted tyrosines, wherein the substituted tyrosine comprises a keto group (such as an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Example phenylalanine analogs include, but are not limited to, para-substituted phenylalanines, ortho-substituted phenyalanines, and meta-substituted phenylalanines, wherein the substituent comprises a keto group, a hydroxy group, a methoxy group, a methyl group, an allyl group, or an aldehyde, or the like. Specific examples of unnatural amino acids include, but are not limited to, a p-acetyl-L-phenylalanine, a m-acetyl-phenylalanine, a p-acyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided in, for example, FIG. 1 herein and FIGS. 16, 17, 18, 19, 26, and 29 of WO 2002/085923, supra.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923, supra, Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials., Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L- and D-α-Amino-Adipic Acids, L-α-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also WO 2002/085923.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., the application entitled "Glycoprotein synthesis," application Ser. No. 10/686,944 filed on Oct. 15, 2003; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc. (available on the world wide web at www.maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly DesignPath™, developed by Genencor (available on the world wide web at genencor.com) is optionally used for metabolic pathway engineering, e.g., to engineer a pathway to create a keto amino acid in a cell. This technology reconstructs existing pathways in host organisms using a combination of new genes, e.g., identified through functional genomics, and molecular evolution and design. Diversa Corporation (available on the world wide web at diversa.com) also provides technology for rapidly screening libraries of genes and gene pathways, e.g., to create new pathways.

Typically, the unnatural amino acid produced with an engineered biosynthetic pathway of the invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Nucleic Acid and Polypeptide Sequence and Variants

As described above and below, the invention provides for nucleic acid polynucleotide sequences, e.g., O-tRNAs and O-RSs, and polypeptide amino acid sequences, e.g., O-RSs, and, e.g., compositions and methods comprising said sequences. Examples of said sequences, e.g., O-tRNAs and O-RSs are disclosed herein (see Table 2, e.g., SEQ ID NO. 1-21). However, one of skill in the art will appreciate that the invention is not limited to those sequences disclosed herein, e.g., the Examples. One of skill will appreciate that the invention also provides many unrelated sequences with the functions described herein, e.g., encoding an O-tRNA or an O-RS.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interests of the invention with one or more selector codon. In addition, polynucleotides of the invention include, e.g., a polynucleotide comprising a nucleotide sequence as set forth in SEQ ID NO.: 1-17, 21; a polynucleotide that is complementary to or that encodes a polynucleotide sequence thereof. A polynucleotide of the invention also includes a polynucleotide that encodes an amino acid sequence comprising SEQ ID NO.: 18-20. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a sequence of SEQ ID NOs: 1-17 and/or 21, (but is other than a naturally occurring polynucleotide). A polynucleotide also includes an artificial polynucleotide that is, e.g., at least 75%, at least 80%, at least 90%, at least 95%, at least 98% or more identical to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively keto amino acid of the same conservative substitution group. Finally, the addition of sequences that do not alter the encoded activity of a nucleic acid molecule, such as the addition of a non-functional sequence, is a conservative variation of the basic nucleic acid.

Conservative substitution tables providing functionally similar amino acids are well known in the art. The following sets forth example groups that contain natural amino acids that include "conservative substitutions" for one another.

Conservative Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) | Valine (V) |
| 6 | Phenylalanine (F) | Tyrosine (Y) | Tryptophan (W) |

Nucleic Acid Hybridization

Comparative hybridization can be used to identify nucleic acids of the invention, such as SEQ ID NO.: 1-17, 21, including conservative variations of nucleic acids of the invention, and this comparative hybridization method is a preferred method of distinguishing nucleic acids of the invention. In addition, target nucleic acids which hybridize to a nucleic acid represented by any of SEQ ID NO: 1-17, 21 under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, infra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see Sambrook, supra, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra, and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any previously known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more keto amino acid, e.g. unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or subsequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information [online].NCBI, 2002 [retrieved Jan., 2002]. Retrieved from the Internet: <URL: www.ncbi.nlm.nih.gov/>. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotides and polypeptides of the invention and used in the invention can be manipulated using molecular biological techniques. General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include keto amino acids (and, optionally, another unnatural amino acids), orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode a keto amino acid and/or another unnatural amino acid in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of Bacteria and Bacteriophages useful for cloning is provided, e.g., by the ATCC, e.g., *The ATCC Catalogue of Bacteria and Bacteriophage* (1996) Ghema et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Proteins or polypeptides of interest with at least one keto amino acid are a feature of the invention. The invention also includes polypeptides or proteins with at least keto amino acid produced using the compositions and methods of the invention. One advantage of keto amino acids is that they can participate in a variety of chemical reactions. The carbonyl group reacts readily with, e.g., hydrazides, hydroxylamines, semicarbazides, and/or the like, under mild conditions in aqueous solution, and forms, e.g., hydrazone, oxime, and semicarbazone linkages, respectively, which are stable under physiological conditions. See, e.g., Jencks, W. P. (1959), supra; Shao, J. & Tam, J. P. (1995), supra. Through the keto amino acid, proteins can be selectively modified or labeled with a wide variety of other hydrazide or hydroxylamine derivatives (including sugars, fluorescence labels, biotin derivatives, spin labels, metal chelators, crosslinking agents, polyethers, fatty acids, toxins, etc.), e.g., to produce probes of protein structure and function, to generate proteins with enhanced catalytic or therapeutic properties, or for the development of bioassays using either immobilized or soluble proteins. See, e.g., the application entitled "Glycoprotein synthesis," application Ser. No. 10/686,944 filed on Oct. 15, 2003. In certain embodiments of the invention, an excipient (e.g., a pharmaceutically acceptable excipient) can be present with the protein. Optionally, a protein of the invention will include a post-translational modification.

Methods of producing a protein in a cell with a keto amino acid at a specified position are also a feature of the invention. For example, a method includes growing, in an appropriate medium, the cell, where the cell comprises a nucleic acid that comprises at least one selector codon and encodes a protein, providing the keto amino acid, and incorporating the keto amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the keto amino acid. In certain embodiments, the O-RS preferentially aminoacylates the O-tRNA with an efficiency of at least about, e.g., a 45%, a 50%, a 60%, a 75%, a 80%, or a 90% or more efficiency of the efficiency of a polypeptide comprising an amino acid sequence of SEQ ID NO.: 18 with a keto amino acid. A protein produced by this method is also a feature of the invention.

The invention also provides compositions that include proteins, where the proteins comprise a keto amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in a keto amino acid being incorporated into a protein. WO 2002/085923, supra, describes this process and is incorporated herein by reference. For example, when an O-tRNA/O-RS pair is introduced into a host, e.g., *Escherichia coli*, the pair leads to the in vivo incorporation of keto amino acid, which can be exogenously added to the growth medium, into a protein, in response to a selector codon. Optionally, the compositions of the present invention can be in an in vitro translation system, or in an in vivo system(s).

A cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises a keto amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nl to about 100 L). The production of large quantities (e.g., greater that that typically possible with other methods, e.g., in vitro translation) of a protein in a cell including at least one keto amino acid is a feature of the invention.

The incorporation of a keto amino acid can be done to, e.g., tailor changes in protein structure and/or function, e.g., to change size, acidity, nucleophilicity, hydrogen bonding, hydrophobicity, accessibility of protease target sites, target access to a protein moiety, etc. Proteins that include a keto amino acid can have enhanced or even entirely new catalytic or physical properties. For example, the following properties are optionally modified by inclusion of a keto amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one keto amino acids are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology*, 4:645-652.

In one aspect of the invention, a composition includes at least one protein with at least one, e.g., at least two, at least three, at least four, at least five, at least six, at least seven, at least eight, at least nine, or at least ten or more unnatural amino acids, e.g., keto amino acids and/or other unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein substituted with the keto amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different, or a combination of multiple unnatural amino acids of the same kind with at least one different unnatural amino acid.

Essentially any protein (or portion thereof) that includes a keto amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more keto amino acid. Examples of therapeutic, diagnostic, and other proteins that can be modified to comprise one or more keto amino acid can be found, but not limited to, those in WO 2002/085923, supra. Examples of therapeutic, diagnostic, and other proteins that can be modified to comprise one or more keto amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO", representing a preferred target for modification by the incorporation of one or more unnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of keto amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more keto amino acids) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one keto amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many proteins that can incorporate a keto amino acid are commercially available (see, e.g., the Sigma BioSciences 2002 catalogue and price list), and the corresponding protein sequences and genes and, typically, many variants thereof, are well-known (see, e.g., Genbank). Any of them can be modified by the insertion of one or more keto amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, e.g., keto amino acids), specificity, reduction of $LD_{50}$ or other side effects, ability to enter the body through the gastric tract (e.g., oral availability), or the like. Examples of relevant diagnostic properties include shelf half-life, stability, diagnostic activity, detectability, specificity, or the like. Examples of relevant enzymatic properties include shelf half-life, stability, enzymatic activity, production capability, specificity, or the like.

A variety of other proteins can also be modified to include one or more keto amino acid of the invention. For example, the invention can include substituting one or more natural amino acids in one or more vaccine proteins with a keto amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., Plasmodia), rhizopods (e.g., *Entamoeba*) and flagellates (*Trypano-* soma, *Leishmania, Trichomonas, Giardia,* etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (–) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for keto amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a keto amino acid. For example, a nucleic acid for a protein of interest is mutagenized to include one or more selector codon, providing for the insertion of the one or more keto amino acids. The invention includes any such variant, e.g., mutant, versions of any protein, e.g., including at least one keto amino acid. Similarly, the invention also includes corresponding nucleic acids, i.e., any nucleic acid with one or more selector codon that encodes one or more keto amino acid.

To make a protein that includes a keto amino acid, one can use host cells and organisms that are adapted for the in vivo incorporation of the keto amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., comprising keto amino acids in the case of proteins synthesized in the translation systems herein, or, e.g., in the case of the novel synthetases, novel sequences of standard amino acids), the polypeptides also provide new structural features, which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology,* 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual,* Cold Spring Harbor Publications, New York, for a standard description of antibody generation, immunoassay formats and conditions that can be used to determine specific immunoreactivity. Additional details on proteins, antibodies, antisera, etc. can be found in WO 2002/085923, supra.

Kits

Kits are also a feature of the invention. For example, a kit for producing a protein that comprises at least one keto amino acid in a cell is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes a keto amino acid. In another embodiment, the kit further comprises instructional materials for producing the protein.

EXAMPLES

The following examples are offered to illustrate, but not to limit the invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Site-Specific Incorporation of a Keto Amino Acid into Proteins

Although the carbonyl group is the most versatile of the functional groups in organic chemistry, it is absent in the genetically encoded amino acids. To overcome this natural limitation on protein biosynthesis, an orthogonal tRNA-synthetase pair was evolved that makes possible the in vivo incorporation of a keto amino acid, p-acetyl-L-phenylalanine, into proteins in *E. coli* with high translational fidelity in response to the amber nonsense codon. To demonstrate the utility of this novel amino acid, a protein was selectively modified in vitro with a small molecule fluorophore and biotin derivative. This new genetically encoded amino acid should greatly expand the ability to manipulate protein structure and function both in vitro and in living cells.

The genetic codes of all known organisms encode the same common twenty amino acids as building blocks for the biosynthesis of proteins. The side chains of these amino acids comprise a surprisingly limited number of functional groups—nitrogen bases, carboxylic acids and amides, alcohols, and a thiol group (and in rare cases, selenocysteine (see, e.g., Bock, A., Forchhammer, K., Heider, J., Leinfelder, W., Sawers, G., Veprek, B. & Zinoni, F. (1991) *Mol. Microbiol.* 5:515-520) or pyrrolysine (see, e.g., Srinivasan, G., James, C. M. & Krzycki, J. A. (2002) *Science* 296:1459-1462; Hao, B., Gong, W., Ferguson, T. K., James, C. M., Krzycki, J. A. & Chan, M. K. (2002) *Science* 296:1462-1466)), the remainder being simple alkanes or hydrophobic groups. The ability to augment the genetically encoded amino acids with new amino acids, for example, amino acids with metal chelating, fluorescent, redox active, photoactive or spin-labeled side chains, would significantly enhance the ability to manipulate the structures and functions of proteins and perhaps living organisms themselves. Recently, it was reported that by adding new components to the translational machinery of *Escherichia coli*, one could site-specifically incorporate with high fidelity a number of unnatural amino acids into proteins in vivo. See, e.g., Wang, L., Brock, A., Herberich, B. & Schultz, P. G. (2001) *Science* 292:498-500; Wang, L., Brock, A. & Schultz, P. G. (2002) *J. Am. Chem. Soc.* 124:1836-1837; and, Zhang, Z., Wang, L., Brock, A. & Schultz, P. G. (2002) *Angew. Chem. Int. Ed. Engl.* 41:2840-2842. This approach can be generalized to add a keto containing amino acid to the genetic code of, e.g., *E. coli*, and that the unique reactivity of the keto group can be used to selectively modify proteins in vitro with a wide variety of agents.

The keto group is ubiquitous in organic chemistry, and participates in a large number of reactions from addition and decarboxylation reactions to aldol condensations. Moreover, the unique reactivity of the carbonyl group allows it to be selectively modified with hydrazide and hydroxylamine derivatives in the presence of the other amino acid side chains. See, e.g., Cornish, V. W., Hahn, K. M. & Schultz, P. G. (1996) *J. Am. Chem. Soc.* 118:8150-8151; Geoghegan, K. F. & Stroh, J. G. (1992) *Bioconjug. Chem.* 3:138-146; and, Mahal, L. K., Yarema, K. J. & Bertozzi, C. R. (1997) *Science* 276:1125-1128. Although present in cofactors (see, e.g., Begley, T. P., Kinsland, C., Taylor, S., Tandon, M., Nicewonger, R., Wu, M., Chiu, H., Kelleher, N., Campobasso, N. & Zhang, Y. (1997) in *Top. Curr. Chem.*, eds. Leeper, F. J. & Vederas, J. C. (Springer-Verlag, New York), Vol. 195, pp. 93-142), metabolites (see, e.g., Diaz, E., Ferrandez, A., Prieto, M. A. & Garcia, J. L. (2001) *Microbiol. Mol. Biol. Rev.* 65:523-569) and as a posttranslational modification to proteins (see, e.g., Okeley, N. M. & van der Donk, W. A. (2000) *Chem. Biol.* 7, R159-R171), this important functional group is absent from the side chains of the common amino acids. In order to genetically encode this functional group in *E. coli* in the form of p-acetyl-L-phenylalanine, a tRNA-synthetase pair was evolved that is capable of inserting this amino acid site-specifically into proteins in *E. coli* in response to an amber nonsense codon. Importantly this tRNA-synthetase pair is orthogonal to its counterparts for the common 20 amino acids, i.e., the orthogonal synthetase aminoacylates the orthogonal tRNA with the unnatural amino acid only, and the resulting acylated tRNA inserts the unnatural amino acid only in response to the amber codon.

Materials and Methods

Preparation of p-acetyl-L-phenylalanine: Fmoc-4-acetyl-L-phenylalanine was purchased from RSP Amino Acid Analogues, Inc. (Worcester, Mass.). This compound (1.0 g, 2.3 mmol) was stirred with 4 mL of piperidine (20% in DMF) for 2 hours at room temperature. The solvent was evaporated to obtain white powder. The solid was then resuspended in 10 mL of cold water (0.1% TFA), and the supernatant was collected by filtration. Preparative reverse-phase HPLC (Microsorb C18, Rainin Instrument Co., Inc., Woburn, Mass.) was used to separate the desired product from the reaction mixture (5-30% $CH_3CN$ in $H_2O$ with 0.1% TFA over 30 min). The eluant ($t_R$=12 min) was lyophilized to a obtain white solid (0.45 g, 88%). $^1$HNMR ($D_2O$): δ 7.85-7.28 (m, 4H), 4.23 (dd, 1H, 5.4 Hz), 3.2 (m, 2H), 2.7 (s, 3H). LRMS, calcd for $C_{11}H_{13}NO_3$ (M++1): 208.09. Found (ESI): 208.47.

Synthesis of p-acetyl-(±)-phenylalanine: See, e.g., Cleland, G. H. (1969) *J. Org. Chem.* 34:744-747. NBS (N-bromosuccinimide) was recrystallized prior to usage. NBS (18.5 g, 105 mmol) was added to a stirred solution of 4-methyl acetophone (13.4 g, 100 mmol) in 400 mL of carbon tetrachloride, followed by the addition of AIBN (2',2'-azobisiosbutyronitrile) (0.43 g, 2.5 mmol). The reaction mixture was then heated to reflux for 4 hours. After completion of reaction (TLC: δ: 1/hexanes:EtOAc), the solution was washed with water (1×100 mL), 1 M aqueous HCl (3×100 mL), 0.5% aqueous $NaHCO_3$ (3×100 mL) and brine (1×100 mL). The organic layer was collected and dried over anhydrous $MgSO_4$, and solvent was evaporated to obtain a yellow solid which was recrystallized with hexanes to afford the desired 1-(4-bromoethyl-phenyl)thanone as solid (16.8 g, 78%). Dry ethanol (50 ml) was added dropwise to pentane-washed sodium pieces (2.3 g, 0.1 mol) under argon atmosphere over 15 minutes and the solution was stirred for another 15 minutes. Solid diethyl acetamidomalonate (2.7 g, 10 mmol) was then added over 30 minutes with stirring, followed by the dropwise addition of 1-(4-bromoethyl-phenyl)thanone (2.1 g, 10 mmol) in dry ethanol over 90 minutes. After the mixture was heated to reflux overnight and cooled, diethyl ether (150 mL) and water (100 mL) were added to the solution. The organic layer was separated and washed successively with 0.5% $NaHCO_3$ (3×100 mL) and brine (1×100 mL). After drying over anhydrous $MgSO_4$, solvent was removed in vacuo to afford a brown gummy solid. Hexanes-dichloromethane (4:1) was added to the residue, and the insoluble material was filtered out and washed exhaustively with 10:1 dichloromethane-benzene to afford 2-acetylamino-2-(4-acetyl-benzyl)malonic acid diethyl ester as a yellow solid (3.3 g, 95% crude yield). This compound was stirred with 4 M HCl in dioxane overnight. The mixture was then evaporated to dryness and recrystallized with water to afford p-acetyl-(±)-phenylalanine (13.2 g, 64% overall yield) as white solid. $^1$HNMR (400 MHz, $D_2O$): δ 7.85-7.28 (m, 4H), 4.27 (dd, 1H, 5.4 HZ), 3.30 (m, 2H), 2.68 (s, 3H). $^{13}$C NMR (400 MHz, $D_2O$): δ 195.8, 174.3, 145.9, 133.1, 128.9, 127.8, 60.2, 38.3, 26.5. LRMS, calcd for $C_{11}H_{13}NO_3$ (M$^+$+1): 208.09. Found (ESI): 208.07.

Mutant synthetase evolution: The positive selection was carried out in the presence of 1 mM p-acetyl-L-phenylalanine as described. See, e.g., Wang, L., Brock, A., Herberich, B. & Schultz, P. G. (2001) *Science* 292:498-500. For the negative selection, plasmid pLWJ17B3 was used to express the mutRNA$^{Tyr}_{CUA}$ (as known herein as "mutRNATyr") under the control of the lpp promoter and rrnC terminator, and the barnase gene with three amber codons at Gln2, Asp44, and Gly65 under the control of arabinose promoter. After the positive selection in chloramphenicol, pBK plasmids encoding mutant TyrRS were isolated and transformed into *E. coli* DH10B competent cells harboring pLWJ17B3. Cells were grown on LB (Luria-Bertani) plates containing 0.2% arabinose, 50 μg/ml kanamycin, and 35 μg/ml chloramphenicol. After 8 hours, cells were removed from the plate, and pBK plasmids were purified for further rounds of selection. After 3 positive selections alternating with 2 negative selections, eleven mutant TyrRS were identified that afforded an $IC_{50}$ value of 9 μg/ml chloramphenicol in the absence of p-acetyl- L-phenylalanine and 120 µg/ml chloramphenicol in the presence of p-acetyl-L-phenylalanine. The protein sequences of these mutant TyrRS converged on 3 independent clones LW1, LW5 and LW6, although the codon usage of each mutant TyrRS differs.

Protein expression and purification: Plasmid pLEIZ was used to express the Z-domain gene with an amber codon at the $7^{th}$ position and a COOH-terminal His6 tag under the control of a bacteriophage-T5 promoter and to terminator, and the mutRNA$^{Tyr}_{CUA}$ gene under the control of the lpp promoter and rrnC terminator. The mutant synthetase gene isolated from clone LW1 (LW1RS) was encoded in plasmid pBKLW1RS under the control of the constitutive E. coli GlnRS promoter and terminator. E. coli DH10B cells cotransformed with pLEIZ and pBK-LW1RS were grown in minimal media containing 1% glycerol and 0.3 mM leucine (GMML media) with 25 µg/mL kanamycin, 34 µg/mL of chloramphenicol, and 1.0 mM p-acetyl-(±)-phenylalanine. When cells reach an OD$_{600}$ of 0.5, isopropyl-β-D-thiogalactopyranoside (IPTG) (1 mM) was added to induce protein expression. After 5 hours, cells were pelleted and the protein was purified by Ni$^{2+}$ affinity chromatography under denaturing conditions according to the manufacturer's protocol (Qiagen, Valencia, Calif.). Proteins were then desalted with a PD-10 column (Amersham Pharmacia, Piscataway, N.J.) and eluted in water. The yield of protein was measured by Bradford assay (BCA kit, Biorad, Hercules, Calif.). Aliquots of protein were used for SDS-PAGE and mass spectrometry.

In vitro protein modification with fluorescein hydrazide and biotin hydrazide: The purified wt and mutant Z domain proteins were exchanged into 1×PBS buffer (100 mM potassium phosphate, pH 6.5, 0.5 M sodium chloride) by dialysis. Fluorescein hydrazide 1 (Molecular Probe, Eugene, Oreg.) or biotin hydrazide 2 (Molecular Probe, Eugene, Oreg.) was dissolved in DMF, and added into 0.5 mg of each protein in silanized eppendorff tubes to a final concentration of 1 mM. PBS buffer (pH 6.5) was added to bring the final volume to 0.5 ml. The reaction mixture was kept at 25° C. for 18 hours. Unreacted dye or biotin was removed from the protein using a PD-10 column (Amersham Pharmacia, Piscataway, N.J.), and proteins were eluted with 1×PBS buffer. To determine the labeling efficiency, the labeling reaction solution was first desalted with a PD-10 column, and protein was eluted with PBS buffer. The protein sample was then analyzed by reverse-phase HPLC (Agilent ZORBAX SB-C18, 4.6 mm×250 mm, flow rate 1.0 mL/min, 10→40% CH$_3$CN in aqueous 50 mM TEAA, pH 7.0 over 70 min). The retention time ($t_R$) for mutant Z domain without labeling was 39.3 min; the $t_R$ for fluorescein hydrazide labeled mutant Z domain was 40.7 min; the $t_R$ for biotin hydrazide labeled mutant Z domain was 40.9 min.

Fluorescence spectrum measurement: All fluorescence emission spectra were recorded using a FluoroMax-2 fluorometer with excitation at 490 nm; excitation and emission bandpass of 4 nm and 4 nm, respectively; a PMT voltage of 950 V; and at a scan rate of 1 nm/sec. Ten ng of each labeled protein were used. The reported spectra represent an average of 3 scans.

Results

A keto amino acid: The keto group provides a unique chemical reactivity not present in the common twenty amino acids due to its ability to participate in addition reactions involving either the carbonyl group or the acidic Cα position. This group also provides an alternative to the natural amino acid cysteine for the selective modification of proteins with a large variety of chemical reagents. The reactive thiol group of cysteine has been extensively used to attach various biophysical probes to proteins. See, e.g., Creighton, T. E. (1986) Methods Enzymol. 131:83-106; Altenbach, C., Marti, T., Khorana, H. G. & Hubbell, W. L. (1990) Science 248:1088-92; Brinkley, M. (1992) Bioconjug. Chem. 3:2-13; Giuliano, K. A., Post, P. L., Hahn, K. M. & Taylor, D. L. (1995) Annu. Rev. Biophys. Biomol. Struct. 24:405-34; Mannuzzu, L. M., Moronne, M. M. & Isacoff, E. Y. (1996) Science 271:213-6; Griffin, B. A., Adams, S. R. & Tsien, R. Y. (1998) Science 281:269-272; Llopis, J., Adams, S. R., McCaffery, J. M., Teter, K., Kulomaa, M. S., Machen, T. E., Moore, H. P., Tsien, R. Y. & Griffin, B. A. (2000) Methods Enzymol. 327:546-64; and, Gaietta, G., Deerinck, T. J., Adams, S. R., Bouwer, J., Tour, O., Laird, D. W., Sosinsky, G. E., Tsien, R. Y. & Ellisman, M. H. (2002) Science 296:503-7. Unfortunately, the labeling of single cysteine residues is often complicated by the presence of more than one accessible cysteine residue in a protein, as well as exchange reactions of the resulting disulfide in the presence of free thiol. Therefore, the availability of a nonproteinogenic amino acid with orthogonal reactivity makes possible selective modification of protein in cases where a single cysteine cannot be selectively labeled, where two different labels are needed, and where a disulfide linkage may not be sufficiently stable. The carbonyl group reacts readily with hydrazides, hydroxylamines, and semicarbazides under mild conditions in aqueous solution, and forms hydrazone, oxime, and semicarbazone linkages, respectively, which are stable under physiological conditions. See, e.g., Jencks, W. P. (1959) J. Am. Chem. Soc. 81, 475-481; Shao, J. & Tam, J. P. (1995) J. Am. Chem. Soc. 117:3893-3899.

Several methods have been developed to selectively incorporate the carbonyl group into peptides and proteins. Initially, an aldehyde was introduced at the N-termini of peptides by oxidizing N-terminal serine or threonine with periodate, followed by coupling to biotin and fluorescent reporters through a hydrazone linkage. See, e.g., Geoghegan, K. F. & Stroh, J. G. (1992) Bioconjug. Chem. 3:138-146. This method is, however, restricted to the N-terminal modification of proteins. Solid phase peptide synthesis was later employed for the preparation of peptide segments containing either a hydrazide or hydroxylamine, which subsequently react with a branched aldehyde core matrix to form peptide dendrimers (see, e.g., Shao, J. & Tam, J. P. (1995) J. Am. Chem. Soc. 117:3893-3899; Rose, K. (1994) J. Am. Chem. Soc. 116:30-33), or with a keto containing peptide segment to form synthetic proteins (see, e.g., Canne, L. E., Ferre-D'Amare, A. R., Burley, S. K. & Kent, S. B. H. (1995) J. Am. Chem. Soc. 117:2998-3007). This approach is generally applicable to peptides or small proteins of less than 100 residues, but is limited by the difficulties associated with the synthesis of large peptides or proteins.

An in vitro biosynthetic method has also been used to incorporate the keto group into proteins. See, e.g., Cornish, V. W., Hahn, K. M. & Schultz, P. G. (1996) J. Am. Chem. Soc. 118:8150-8151. In this method, the unnatural amino acid containing the keto group is chemically acylated to an amber suppressor tRNA. When the acylated tRNA and the mutant gene are combined in an in vitro extract capable of supporting protein biosynthesis, the unnatural amino acid is selectively incorporated in response to a UAG codon. This method requires the suppressor tRNA to be chemically aminoacylated with the unnatural amino acid in vitro, and the acylated tRNA is consumed as a stoichiometric reagent during translation and cannot be regenerated, resulting in low protein yields. By evolving an orthogonal tRNA-synthetase pair with specificity for p-acetyl-Lphenylalanine, a keto amino acid can be incorporated into proteins in response to the UAG codon directly in living E. coli cells. There is no size limitation on the target protein as long as it can be expressed in *E. coli*, and large amounts of the mutant protein can be expressed. Moreover, as long as the labeling reagent is cell permeable and nontoxic, the label can be selectively introduced in whole cells.

Evolution of mutant synthetases with specificities for p-acetyl-L-phenylalanine: The *Methanococcus jannaschii* tyrosyl-tRNA synthetase (TyrRS) and a mutant tyrosine amber suppressor tRNA (mutRNA$^{Tyr}_{CUA}$) were used as the starting point for the generation of the orthogonal tRNA-synthetase pairs. Previously, this pair was shown to be orthogonal in *E. coli*. See, e.g., Wang, L., Magliery, T. J., Liu, D. R. & Schultz, P. G. (2000) *J. Am. Chem. Soc.* 122:5010-5011; and, Wang, L. & Schultz, P. G. (2001) *Chem. Biol.* 8:883-890. To change the amino acid specificity of the TyrRS so that it charges p-acetyl-Lphenylalanine and not any of the common 20 amino acids, a library of *M. jannaschii* TyrRS mutants was generated and screened. The crystal structure of the homologous *Bacillus stearothermophilus* TyrRS (see, e.g., Brick, P., Bhat, T. N. & Blow, D. M. (1989) *J. Mol. Biol.* 208:83-98.) was used to identify those residues that are within 6.5 Å of the para position of the aryl ring of bound tyrosine. Five corresponding residues (Tyr32, Glu107, Asp158, Ile159 and Leu162) in the active site of *M. jannaschii* TyrRS were randomly mutated by polymerase chain reaction (PCR) to generate a library 1.6×10$^9$ in size. See, e.g., Wang, L., Brock, A., Herberich, B. & Schultz, P. G. (2001) *Science* 292:498-500. This TyrRS mutant library was first passed through a positive selection in the presence of 1 mM p-acetyl-L-phenylalanine which is based on the suppression of an amber stop codon at nonessential residue (Asp 112) in chloramphenicol acetyl transferase (CAT) gene encoded on plasmid pYC-J17 (see, e.g., Wang, L., Brock, A., Herberich, B. & Schultz, P. G. (2001) *Science* 292:498-500) in *E. coli*. Cells surviving in chloramphenicol must encode a mutant synthetase that aminoacylates the mutRNA$^{Tyr}_{CUA}$ with either a common amino acid(s) or p-acetyl-L-phenylalanine. DNA encoding the mutant synthetases was then isolated and transformed into a negative selection strain expressing the gene of a toxic protein, barnase, containing three amber codons at permissive sites (encoded on plasmid pLWJ17B3). Cells encoding a mutant synthetase that charges the mutRNA$^{Tyr}_{CUA}$ with natural amino acids will produce barnase and die. Because no p-acetyl-L-phenylalanine was added to the growth medium in the negative selection, survivors must encode a synthetase with specificity for the unnatural amino acid. After 3 rounds of positive selection at increasing concentrations of chloramphenicol, alternating with 2 rounds of negative selection, a number of clones emerged whose survival in chloramphenicol was dependent on the addition of p-acetyl-L-phenylalanine. These TyrRS's were characterized using an in vivo assay based on the suppression of the Asp112TAG codon in the CAT gene. See, e.g., Wang, L. & Schultz, P. G. (2001) *Chem. Biol.* 8:883-890. Eleven TyrRS mutants were identified. Cells expressing the selected synthetase and the mutRNA$^{Tyr}_{CUA}$ survived in the absence of p-acetyl-L-phenylalanine on 9 μg/ml chloramphenicol on minimal media plates containing 1% glycerol and 0.3 mM leucine (GMML plate); in the presence of this unnatural amino acid, cells survived in 120 μg/ml chloramphenicol on GMML plates. This result suggests that the selected mutant synthetase has higher activity for p-acetyl-L-phenylalanine than for natural amino acids. Sequencing the DNA of these mutants revealed that they converge on 3 independent mutants on the protein level (LW1, LW5, and LW6), although they have different codon usage for amino acids. The active site mutations of the mutant synthetases are listed in Table 1. Based on the crystal structure of the homologous TyrRS from *B. stearothermophilus*, the conserved side chain of *M. jannaschii* Tyr32 and Asp158 likely form hydrogen bonds with the hydroxyl group of the substrate tyrosine. In the mutant synthetases, Tyr32 is mutated to either Leu or Ala, and Asp158 is mutated to Gly158. These mutations can disfavor the binding of tyrosine and can at the same time create extra room to accommodate the methyl group of p-acetyl-L-phenylalanine.

TABLE 1

AMINO ACID RESIDUES IN THE WT *M. JANNASCHII* (MJ) TYRRS AND THE EVOLVED MUTANT SYNTHETASES WITH SPECIFICITIES FOR P-ACETYL-L-PHENYLALANINE.

| Amino acid residue | 32 | 158 | 159 | 162 | 167 |
|---|---|---|---|---|---|
| wt Mj TyrRS | Tyr | Asp | Ile | Leu | Ala |
| LW1 | Leu | Gly | Cys | Arg | Ala |
| LW5 | Leu | Gly | Thr | Arg | Ala |
| LW6 | Ala | Gly | Gly | Leu | Ile |

Characterization of mutant protein containing p-acetyl-L-phenylalanine: To test the ability of the evolved synthetase and the mutRNA$^{Tyr}_{CUA}$ to selectively incorporate p-acetyl-L-phenylalanine into proteins, an amber stop codon was substituted at a permissive site (Lys7) in the gene for the Z domain of staphylococcal protein A (see, e.g., Nilsson, B., Moks, T., Jansson, B., Abrahmsen, L., Elmblad, A., Holmgren, E., Henrichson, C., Jones, T. A. & Uhlen, M. (1987) *Protein Eng.* 1:107-13) with a COOH-terminal His6 tag. Z domain has a molecular weight of about 7.9 kD, so its mass can be measured with very high accuracy using ion cyclotron resonance mass spectrometry. Cells transformed with the mutRNA$^{Tyr}_{CUA}$, LW1RS and Z domain gene (Lys7TAG) were grown in the presence of 1 mM p-acetyl-(±)-phenylalanine. The addition of the unnatural amino acid did not affect the growth rate of cells. The mutant protein was purified by Ni$^{2+}$ affinity chromatography with an overall isolated yield of 3.6 mg/L in minimal media. For comparison, the yield of Z domain was 9.2 mg/L in minimal media when the mutant TyrRS was replaced with the wild-type (wt) TyrRS. No Z domain was obtained in the absence of either p-acetyl-(±)-phenylalanine, the mutRNA$^{Tyr}_{CUA}$ or LW1RS (FIG. 1), indicating a very high fidelity in the incorporation of the unnatural amino acid at this site. p-acetyl-Lphenylalanine can also been incorporated into other proteins, e.g., Cdc42. See FIG. 1.

Figure 2A:
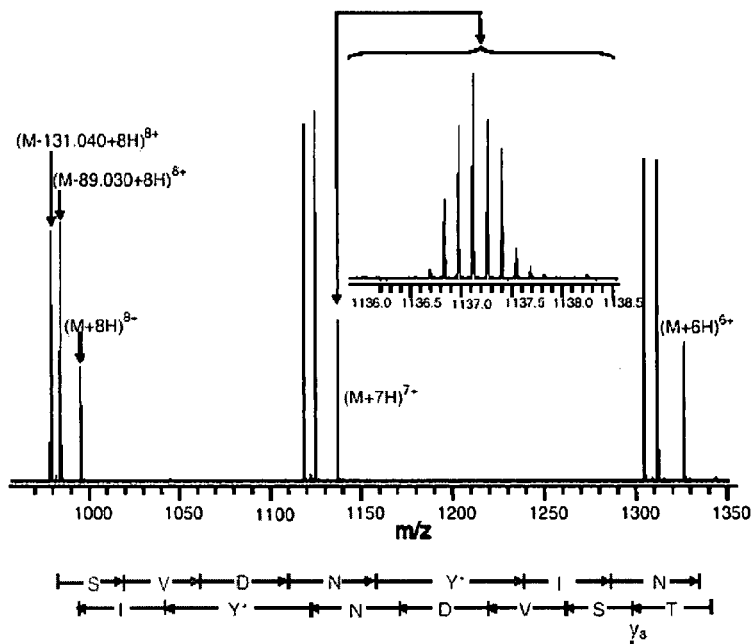
FIG. 2 Panels (A) and (B) illustrate (A) high resolution FT-ICR mass spectrum of the intact mutant protein Z domain containing p-acetyl-L-phenylalanine. A series of peaks corresponding to different charge states of the protein can be observed. In each series, there are three peaks corresponding to the protein without the first methionine, its acetylated form, and the intact protein as labeled for the $8^+$ charge state. The insert is the expansion of the molecular peak of the Z domain protein from the $7^+$ isotopic cluster. (B) illustrates tandem mass spectrum of the $NH_2$-terminal peptide MTSVDNY*INK. The partial sequence of TSVDNY*IN of the peptide containing p-acetyl-L-phenylalanine (Y*) can be assigned from the annotated b and y ion series.
Figure 2B:
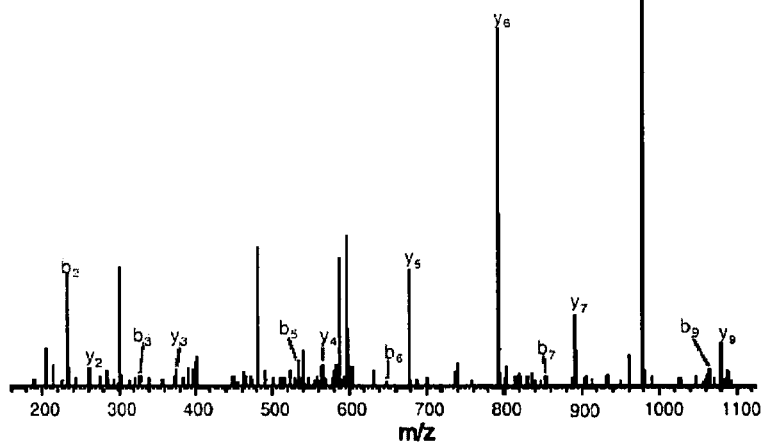

Both the wt Z domain protein expressed by mutRNA$^{Tyr}_{CUA}$/wt TyrRS and the mutant Z domain protein expressed by the mutRNA$^{Tyr}_{CUA}$/LW1RS were analyzed by electrospray ionization Fourier transform ion cyclotron resonance mass spectrometry (FT-ICR MS). For the wt Z domain protein, three peaks were observed with masses corresponding to the intact protein, the protein without the first methionine, and the acetylated form of the protein without the first methionine (confirmed by tandem mass spectrometric analysis of the N-terminal tryptic digested peptide fragment). For the mutant Z domain protein (FIG. 2A), the experimental monoisotopic mass of the intact protein was 7949.893 Da, which is within 2.2 ppm of the theoretical mass of 7949.874 Da. Two other peaks correspond to the protein without the first methionine ($M_{Experimental}$=7818.838 Da, $M_{Theoretical}$=7818.833 Da) and its acetylated form ($M_{Experimental}$=7860.843 Da, $M_{Theoretical}$=7860.844 Da), respectively. No peaks corresponding to mutant proteins with any other amino acid at the amber codon position were observed in the spectra. The signal-to-noise ratio of more than 1500 observed in the intact protein mass spectrum translates to a fidelity for the incorporation of p-acetyl-L-phenylalanine of better than 99.8%. Liquid chromatography tandem mass spectrometry of the tryptic digest was carried out to confirm the sequence of the $NH_2$-terminal peptide. The precursor ion at 606.23 Da, which corresponds to the doubly charged molecular ion of the $NH_2$-terminal tryptic peptide MTSVDNY*INK, was isolated and fragmented with an ion trap mass spectrometer (ITMS). The fragment ion masses could be unambiguously assigned as shown in FIG. 2B, confirming the site-specific incorporation of p-acetyl-L-phenylalanine. These results clearly demonstrate that the evolved synthetase together with the mutRNA$^{Tyr}_{CUA}$ incorporate p-acetyl-L-phenylalanine and not any natural amino acid into the position encoded by the amber codon and at no other positions. See FIG. 2.

Figure 3A:
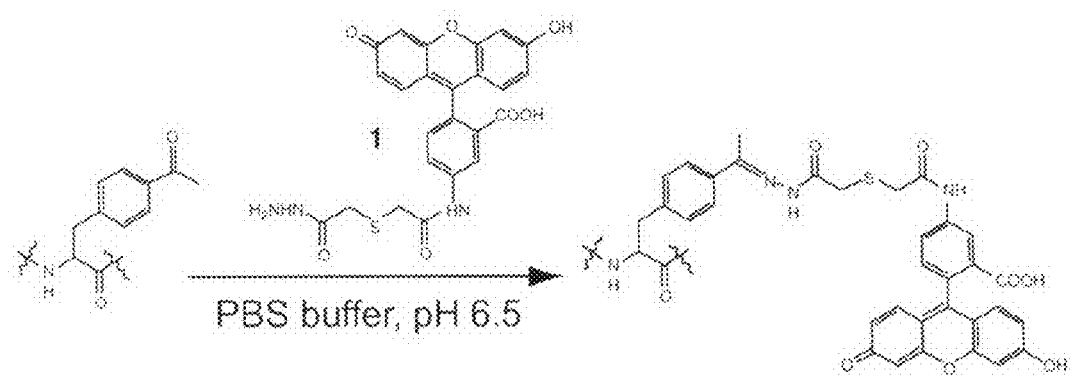
FIG. 3, Panels (A), (B), and (C) illustrate in vitro labeling of mutant Z domain containing p-acetyl-L-phenylalanine with fluorescein hydrazide 1. (A) illustrates labeling reaction of p-acetyl-L-phenylalanine by fluorescein hydrazide 1. (B) illustrates a silver-stained SDS-PAGE (top) analysis and fluorescence imaging (bottom) of wild type (wt) and mutant Z domain labeled with fluorescein hydrazide 1. (C) illustrates fluorescence spectra for wt and mutant Z domain labeled with fluorescein hydrazide 1.
Figure 3B:
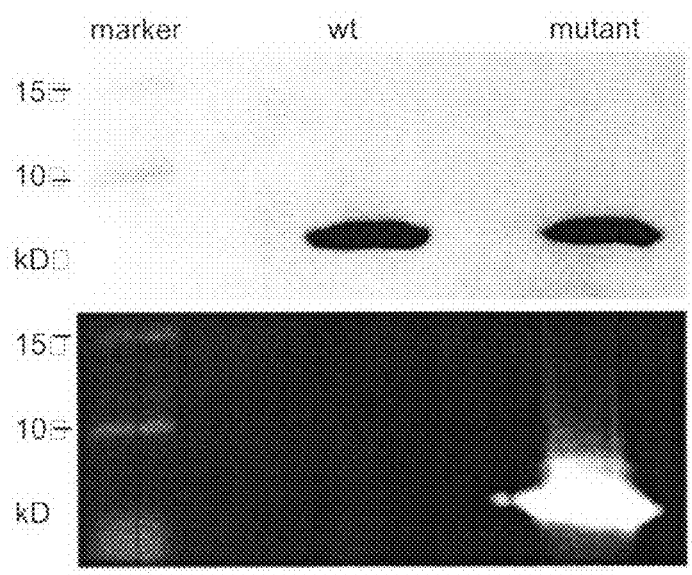
Figure 3C:
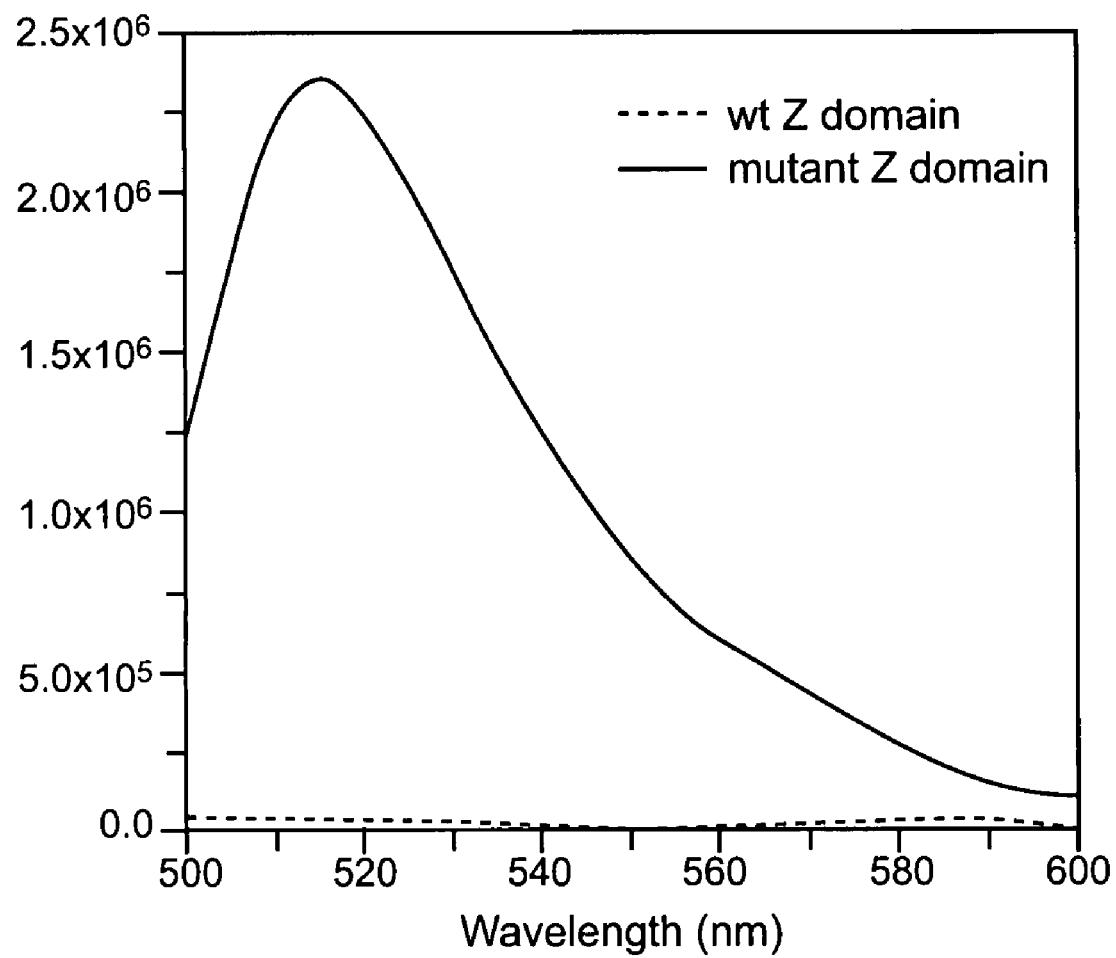

Site-specific protein modification with fluorescein hydrazide: The carbonyl group of p-acetyl-L-phenylalanine can serve as a chemical handle for the site-specific modification of proteins in vitro. The purified mutant p-acetyl-L-phenylalanine Z domain protein (mutant Z domain) and wt Z domain protein were treated with 1 mM fluorescein hydrazide 1 (FIG. 3A) at 25° C. for 18 hours in PBS buffer. After the reaction, proteins were separated from excess fluorescein hydrazide by size exclusion chromatography, and analyzed with SDS-polyacrylamide gel electrophoresis (SDS-PAGE). The gel was first imaged with a fluoroimaging system, and then silver stained (FIG. 3B). The band for mutant Z domain shows a fluorescent signal while no fluorescence can be detected from the wt Z domain band. Aliquots of these two proteins were used to measure the fluorescence spectrum with 490 nm excitation (FIG. 3C). Only the Z domain protein containing p-acetyl-L-phenylalanine shows a fluorescence spectrum similar to that of fluorescein. No fluorescence signal was detected for wt Z domain, indicating that the labeling reaction occurred only between the hydrazide and the ketone, and not any existing functional groups in the wt protein. The labeled product was analyzed with quadrupole time-of-flight mass spectrometry (QTOF MS). An experimental monoisotopic mass of 8425.160 Da ($M_{Theoretical}$=8424.958 Da) was obtained, confirming that the fluorescein hydrazide reacted with the mutant Z domain protein in a molar ratio of 1:1. To determine the labeling extent, the reaction mixture was separated by high performance liquid chromatography (HPLC). The ratio of the peak area of the labeled Z domain over that of the unlabeled Z domain was 90±5%. See FIG. 3.

Figure 4A:
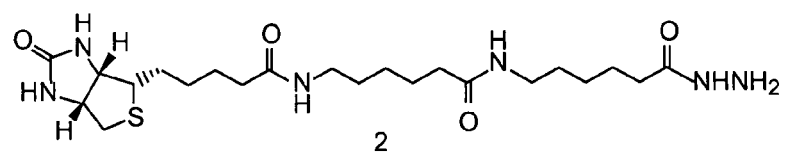
FIG. 4, Panels (A) and (B) illustrate in vitro labeling of mutant Z domain containing p-acetyl-L-phenylalanine with biotin hydrazide 2. (A) illustrates the structure of the biotin hydrazide derivative used, 6-(((6 ((biotinoyl)amino)hexanoyl) amino) hexanoic acid hydrazide (Molecular Probes, Eugene, Oreg.). (B) illustrates a western blot analysis of wt and mutant Z domain labeled by biotin hydrazide 2.
Figure 4B:
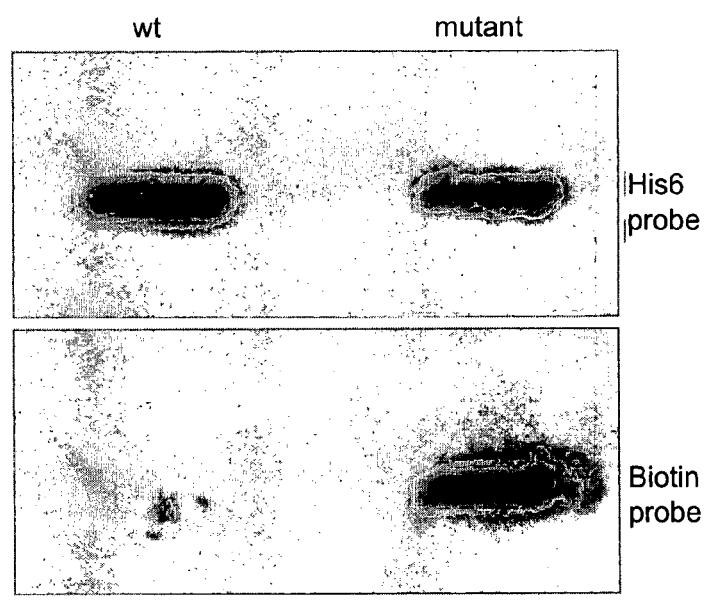

Site-specific protein modification with biotin hydrazide: To demonstrate the generality of this approach, Z domain was labeled with the biotin hydrazide derivative 2 (FIG. 4A). The purified mutant and wt Z domain were treated with 1 mM biotin hydrazide 2 in PBS buffer at 25° C. for 18 hours. After dialysis against PBS buffer to remove excess biotin hydrazide, the proteins were subject to SDS-PAGE. Separated proteins were transferred to nitrocellulose membrane and probed with a biotin-specific avidin-HRP conjugate (FIG. 4B). As expected, only the mutant Z domain containing p acetyl-L-phenylalanine was detected, indicating it was labeled with biotin hydrazide. No signal was observed for wt Z domain. The labeling efficiency was 80±10% as determined by HPLC analysis as described in the fluorescein labeling experiment. The labeled protein was confirmed by QTOF MS ($M_{Experimental}$=8416.236, $M_{Theoretical}$=8416.146 Da) to be the product formed between one molecule of biotin hydrazide and one molecule of mutant Z domain. These experiments demonstrate the excellent specificity of the ketone handle for the in vitro modification of proteins. See FIG. 4.

A novel chemical functional group, the keto group, was site-specifically incorporated into proteins in vivo. This functional group can be selectively and efficiently labeled with fluorescein and biotin in vitro by an orthogonal chemical reaction between the carbonyl group and hydrazide derivatives. For example, using this approach, proteins can be selectively labeled with a wide variety of other hydrazide or hydroxylamine derivatives (including sugars, spin labels, metal chelators, crosslinking agents, polyethers, fatty acids and toxins), either as probes of protein structure and function, to generate proteins with enhanced catalytic or therapeutic properties, or for the development of bioassays using either immobilized or soluble proteins. The ability to site-specifically incorporate an orthogonal chemical handle into proteins directly in a living cell can make possible the in vivo modification of proteins with small molecule fluorophores for the in vivo imaging of protein localization, protein movement and conformational changes in proteins at molecular resolution. In vivo labeling of proteins containing p-acetyl-L-phenylalanine with fluorophores in E. coli can also be done. Finally, it can be determine through either directed or random mutagenesis whether keto amino acids can enhance protein function directly, for example, by forming Schiff base intermediates that participate in catalysis or intra or intermolecular protein crosslinks.

See also corresponding application entitled "Glycoprotein synthesis" application Ser. No. 10/686,944 filed Oct. 15, 2003, which is incorporated herein by reference.

Example 2

In Vivo Incorporation of Meta-Tyrosine Analogues

An orthogonal TyrRS was generated for aminoacylation of the mtRNA$^{Tyr}_{CUA}$ (described in Example 1 of WO 2002/085923) with meta-tyrosine analogues.

Preparation of mutant TyrRS library plasmids: A library of plasmids encoding mutant M. jannaschii TryRSs directed at meta-substituted tyrosine derivatives was constructed, generally following the methods described in Example 1 of WO 2002/085923. Briefly, six residues (Tyr$^{32}$, Ala$^{67}$, His$^{70}$, Gln$^{155}$, Asp$^{158}$, Ala$^{167}$) in the active site of M. jannaschii TyrRS that are within 6.9 Å of the meta-position of the aryl ring of bound tyrosine in the crystal structure of Bacillus stearothermophilus TyrRS were mutated to all 20 amino acids at DNA level using the NNK codon scheme as described in Example 1 above. The constructed plasmid library pBK-lib contained around 1×10$^9$ independent clones.

Evolution of orthogonal tRNA-synthetase pairs for incorporation of m-acetyl phenylalanine: After 3 rounds of positive selection and 2 rounds of negative selection, five candidate clones (SEQ ID NO: 17-21 of WO 2002/085923 and SEQ ID NO: 49-53 of WO 2002/085923) emerged whose survival in chloramphenicol was dependent on the addition of the unnatural amino acid. In the absence of m-acetyl phenylalanine, the IC$_{50}$ of chloramphenicol resistance for cells harboring the one of the three mutant TyrRS plasmids is 20 μg/ml. In the presence of m-acetyl phenylalanine, the IC$_{50}$ of resistance to chloramphenicol for the same cells is 100 μg/ml. The large difference between these two numbers reflects the ability of the selected synthetases to specify the incorporation of m-acetyl phenylalanine over the natural amino acids in the cell. The data for m-methoxy phenylalanine were similar; five clones were isolated (SEQ ID NO:22-26 of WO 2002/085923 and SEQ ID NO: 54-58 of WO 2002/085923).

Protein expression of unnatural amino acid incorporated DHFR: The m-methoxy phenylalanine and m-acetyl phenylalanine synthetases selected above were used to incorporate the relevant unnatural amino acids in response to an amber codon in DHFR as previously described in Example 1 of WO 2002/085923. As a negative control, cells containing both the orthogonal pair of tRNA-synthetase and amber-mutant vector encoding DHFR were grown in the absence of unnatural amino acids. The results of protein expression are shown in FIG. 10 of WO 2002/085923. These results clearly demonstrated the specificity of the orthogonal pair of tRNA-synthetase to incorporate unnatural m-methoxy phenylalanine and m-acetyl phenylalanine. The yields of expressed DHFR protein are approximately 0.5 mg/L of culture in both cases.

In one embodiment, compounds (e.g., hydrazide derivatives) can be used to in vivo label proteins with at least one keto amino acid, e.g., meta-tyrosine analogue.

Example 3

Exemplary O-RSs and O-tRNAs for the Incorporation of Unnatural Amino Acids

An exemplary O-tRNA that mediates the incorporation of a keto amino acid comprises SEQ ID NO.: 21 (See Table 2). Example O-RSs that aminoacylate O-tRNA with keto amino acids include SEQ ID NO.: 18-20 (See Table 2). Examples of polynucleotides include those that encode O-RSs or portions thereof include polynucleotides, e.g., SEQ ID NOs: 1-17 (for the incorporation of other unnatural amino acids), or that encode an amino acid sequence comprising SEQ ID NO.: 18-20 (for the incorporation of keto amino acids).

Example 4

Directed Evolution of the Substrate Specificities of an Aminoacyl-tRNA synthetase Using Fluorescence Activated Cell Sorting Fluorescence-activated cell sorting (FACS) can be used to rapidly screen large libraries of protein variants produced in *Escherichia coli*. Methods are described that employ FACS, along with genetic fluorescence reporters, to direct the evolution of the substrate specificities of a tyrosyl-tRNA synthetase from *Methanococcus jannaschii*. The system utilizes a double-sieve strategy to identify enzyme variants that selectively recognize a novel substrate.

A variety of in vivo selection and screening methods have been developed for the directed evolution of protein function. Typically, in vivo selection strategies involve the identification of new binding or catalytic functions based on their ability to confer a selective growth advantage on the host cell (usually *Escherichia coli*). In vivo screening approaches differ from selections in that screening involves the detection of a desired activity on the basis of its ability to produce an identifiable signal in an activity assay.

For the evolution of enzyme substrate specificity, selection and screening approaches each offer advantages and limitations. Altering the specificity of an enzyme to selectively utilize a new substrate usually requires a "double-sieve" strategy such that activity with the new substrate causes cell survival, while activity with the old substrate causes cell death. Since it is not always easy to link an enzymatic activity to cell survival and death, this requirement limits the generality of such approaches. In contrast, screening approaches require only that an enzymatic activity be linkable to a signal that can be assayed. Screening systems are readily adaptable for use as double-sieves: positive and negative screening identifies enzyme variants that are active in the presence and absence of a substrate, respectively. Moreover, screening stringency can often be varied more readily than selection stringency. Thus, in vivo screening approaches offer the advantage of versatility for evolving the substrate specificity of an enzyme.

On the other hand, selection approaches offer the advantage that the time required to carry out a cycle of selection does not typically scale with the size of the starting library. In contrast, the time required to carry out a cycle of screening increases with the size of the library being screened, which can make screening very large libraries impractical. High-throughput methods can be used to reduce the time requirements for screening large libraries. One such method, fluorescence activated cell sorting (FACS), can be used to rapidly screen individual bacterial cells containing protein variants. See, e.g., Winson, M. K. & Davey, H. M. (2000). *Flow cytometric analysis of microorganisms. Methods* 21:231-240; and, Georgiou, G. (2001). *Analysis of large libraries of protein mutants using flow cytometry. Adv Protein Chem* 55:213-315. Screening can be carried out at a rate of about $10^8$ cells per hour, which is sufficient to cover the size of the largest protein libraries that can currently be constructed in *E. coli*. The primary requirement for using FACS to evolve a desired enzymatic activity is that it be possible to link the activity to the production of a fluorescence signal.

Here, the use of FACS in the directed evolution of substrate specificity is presented for a MjYRS, the tyrosyl-tRNA synthetase from *Methanococcus Jannaschii* (Santoro, S. W., Wang, L., Herberich, B., King, D. S. & Schultz, P. G. (2002). *An efficient system for the evolution of aminoacyl-tRNA synthetase specificity. Nat Biotechnol,* 20:1044-1048). For the synthetase enzyme, a switch in substrate specificity (as opposed to a broadening of specificity) uses a double-sieve strategy. Positive selection pressure favors enzyme variants that recognize the new substrate, e.g., the unnatural amino acid, while negative pressure favors variants that cannot recognize the original substrate. For aminoacyl-tRNA synthetase evolution, a method involving positive selection and negative screening is presented.

Materials & Methods

Figure 5A:
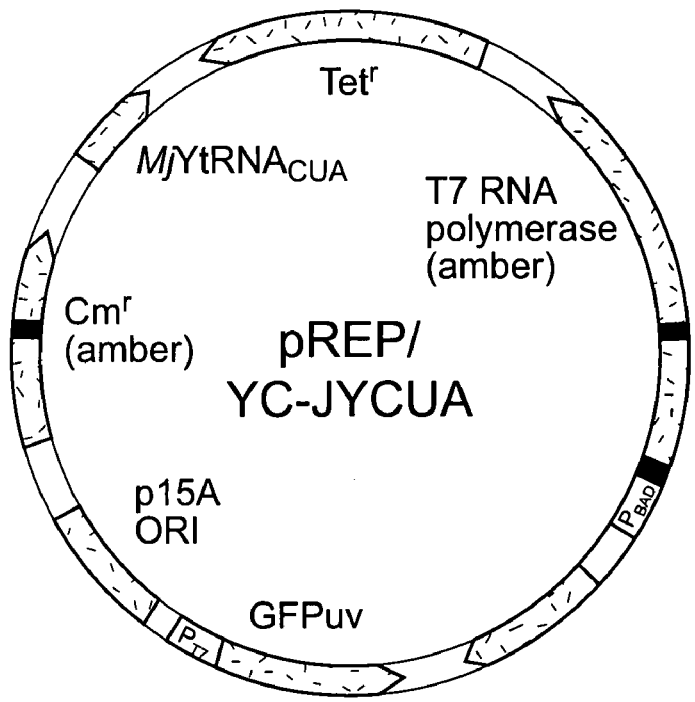
FIG. 5, Panels (A) and (B) illustrate an aminoacyl-tRNA synthetase plasmid system for selection and screening. (A) illustrates plasmid pREP/YC-JYCUA. The amplifiable fluorescence reporter is used for FACS-based screening: T7 RNA polymerase, the gene for which is under control of the ara promoter ($P_{BAD}$), is produced upon suppression of the amber stop codons (black) and drives expression of the GFPuv gene. The chloramphenicol reporter ($Cm^r$) is used for positive selection, conferring bacterial resistance to chloramphenicol upon suppression of the amber stop codon (black). Plasmid pREP/YC-JYCUA contains the $MjYtRNA_{CUA}$ gene, which encodes an orthogonal amber suppressor $tRNA^{Tyr}$ derived from *M. jannaschii*, a p15A origin of replication, and a tetracycline selectable marker ($Tet^r$). (B) illustrates a plasmid pBK-JYRS, which contains the constitutively-expressed tyrosyl-tRNA synthetase gene from *M. jannaschii* (MjYRS), a kanamycin selectable marker ($Kn^r$), and the ColE1 origin of replication. The pBK library plasmids are constructed as outlined under Example 4 using the restriction sites shown.
Figure 5B:
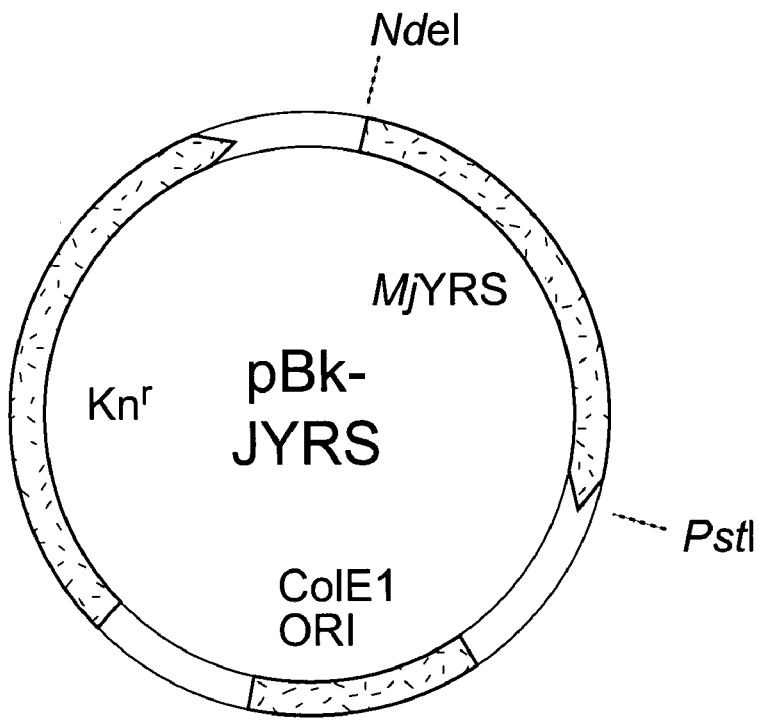

Bacterial strains, genetic constructs, and oligonucleotide primers: The materials used to in the aminoacyl-tRNA synthetase evolution include the following: *E. coli* strain DH10B (Life Technologies); plasmid pREP/YC-JYCUA (FIG. 5A), designed and constructed as previously described (see Santoro, S. W., Wang, L., Herberich, B., King, D. S. & Schultz, P. G. (2002). *An efficient system for the evolution of aminoacyl-tRNA synthetase specificity. Nat Biotechnol,* 20:1044-1048) as a reporter for activity of orthogonal aminoacyl-tRNA synthetase variants in *E. coli*; plasmid pBK-JYA6 (FIG. 5B), designed and constructed as previously described (see Wang, L., Brock, A., Herberich, B. & Schultz, P. G. (2001). *Expanding the genetic code of Escherichia coli. Science* 292:498-500) as a vector for expression of aminoacyl-tRNA synthetase gene variants; PCR fragment libraries of *M. jannaschii* tyrosyl-tRNA synthetase (MjYRS) gene variants were constructed as previously described (see, e.g., Wang, L., Brock, A., Herberich, B. & Schultz, P. G. (2001). *Expanding the genetic code of Escherichia coli. Science* 292:498-500) using a targeted mutagenesis strategy; and, oligonucleotide PCR primers for amplification of MjYRS gene variant libraries (Table 3). Plasmid pREP/YC-JYCUA (FIG. 5A) has the p15A origin of replication, which allows it to replicate simultaneously in *E. coli* with plasmid pBK-JYRS (and variants; FIG. 5B), which has the ColE1 origin of replication. It contains a chloramphenicol acetyl transferase (CAT) reporter that is used as the basis for positive selection and a T7 RNA polymerase (T7 RNAP)/green fluorescent protein (GFPuv) reporter system that is used with FACS to screen against synthetase variants that accept natural amino acids. The fluorescence reporter system also is used to visually and fluorimetrically evaluate synthetase activity based on amino acid incorporation.

TABLE 3

OLIGONUCLEOTIDE PRIMERS FOR PCR AMPLIFICATION

Amplification of MjYRS gene variant libraries
pBK-MjYRSN
5'-GAGGAATCC<u>CATATG</u>GACGAATTTGAAATGATAAAGAG
            NdeI pBK-MJYRSC
5'-CGTTTGAAA<u>CTGCAG</u>TTATAATCTCTTTCTAATTGG
            PstI Other materials used in the directed evolution of substrate specificities of synthetases include the following: restriction enzymes; calf intestinal alkaline phosphatase (CIP); reaction components for PCR (e.g., a thermostable DNA polymerase, PCR buffer, and deoxynucleotide triphosphates (dNTPs) (although Pfu DNA polymerase was used for the methods described here, the Expand kit from Roche has been found to give higher PCR yields, especially for longer PCR products)); PCR purification kit; gel extraction kit; T4 DNA ligase; electroporator and 0.2 cm electroporation cuvettes; Maxiprep plasmid purification kit; agarose and agarose gel electrophoresis equipment; Tris-acetate EDTA (TAE) buffer (40 mM Tris-acetate, 1 mM EDTA (pH 8.3)); ethidium bromide; SOC media; LB media; glucose stock solution (20% in water; sterile-filtered); IPTG (isopropyl-β-D-thio-galactopyranoside) (1 mM in water; should be stored at about −20° C.); PBS (phosphate buffered saline) (10 mM phosphate, 0.14 M NaCl, 2.7 mM KCl (pH 7.4 at 25° C.)); Miniprep plasmid purification kit; ampicillin stock solution (100 mg/mL in water; should be stored at about −20° C.); kanamycin stock solution (35 mg/mL in water; should be stored at about −20° C.); glycerol minimal media with leucine (GMML; contains 1% glycerol and 0.3 mM Leucine); tetracycline stock solution (25 mg/mL in 75% EtOH; should be stored at about −20° C.); arabinose stock solution (20% in water; sterile-filtered); unnatural amino acids stock solution (typically, 0.3 M in 0.3 M HCl or NaOH; should be stored at about −20° C.); glycerol (10% in deionized water; sterile-filtered); and, fluorimeter and quartz cuvette.

Figure 6:
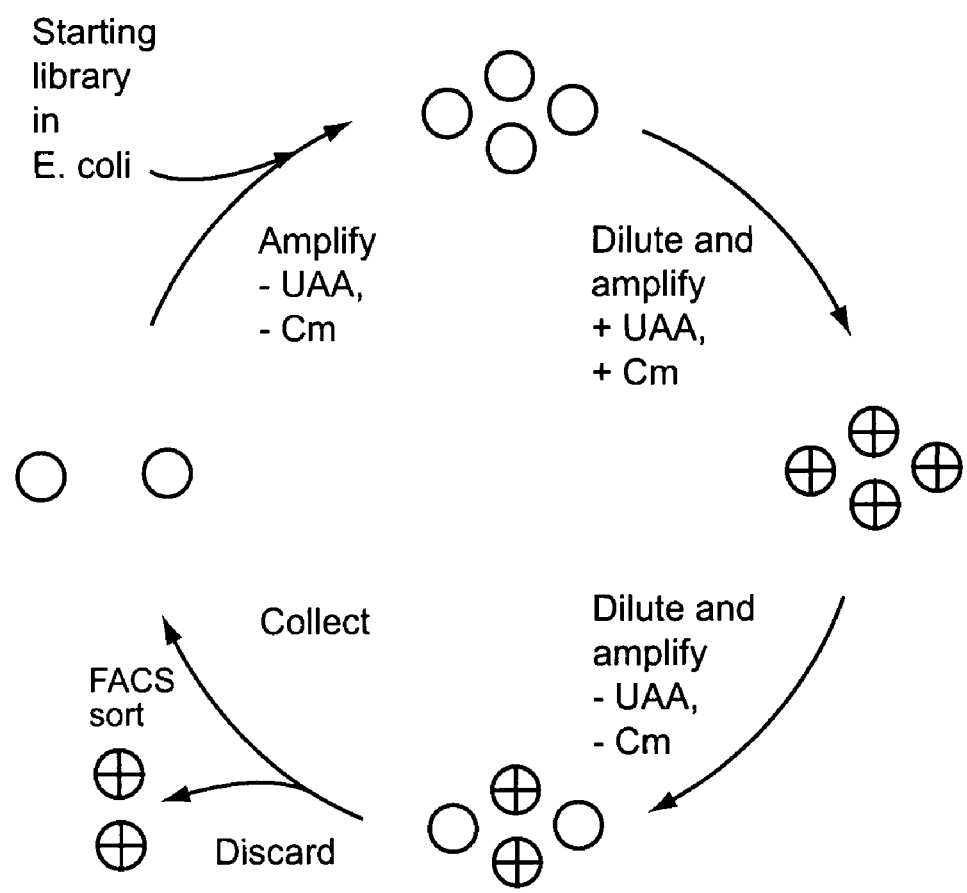
FIG. 6 illustrates an example of a method for the evolution of an aminoacyl-tRNA synthetase using positive selection and negative FACS-based screening. Fluorescent and non-fluorescent cells are shown in crossed circles and white circles, respectively. 'UAA' refers to unnatural amino acid.

Directed evolution of, e.g., a tyrosyl-tRNA synthetase: The following method describes the use of a selection/screening system to identify tyrosyl-tRNA synthetase variants that efficiently and specifically charge an orthogonal tRNA with an unnatural amino acid. The strategy uses a chloramphenicol-based selection to positively enrich variants that recognize the novel amino acid and negative FACS-based screen to eliminate those variants that accept one of the natural amino acids (FIG. 6).

In principle, directed evolution of an aminoacyl-tRNA synthetase can be carried out entirely by FACS-based screening. For such a strategy, the chloramphenicol-based positive selection is replaced with a positive screen in which fluorescent cells grown in the presence of an unnatural amino acid are collected using FACS.

The following steps outline the production of electrocompetent DH10B-DE3 cells harboring the pREP/YC-JYCUA reporter plasmid (FIG. 5A). 25 µL of electrocompetent *E. coli* DH10B cells were transformed with 10 ng of plasmid pREP/YC-JYCUA. Conditions that are recommended by the electroporator manufacturer can be used. The cells should remain cold at all times prior to transformation. Also, the cells should be electroporated as quickly as possible after thawing on ice, as they will lose competency over time. 200 µL of SOC media was immediately added and the cells were allowed to recover with gentle shaking (225 rpm) at 37° C. for 1 hr. Recovered cells were plated on LB agar containing 25 µg/mL tetracycline and incubated at 37° C. overnight. From a single colony, electrocompetent DH10B (pREP/YC-JYCUA) cells were prepared. Efficient plasmid construction comes from high competency in the transformation of *E. coli*, especially when large numbers of transformants are required. Electroporation is a convenient method for transforming *E. coli*; the preparation of electrocompetent *E. coli* strains with transformation efficiencies of $10^8$-$10^{10}$ cfu/µg of supercoiled plasmid DNA is routine. Keep in mind that for non-supercoiled and nicked plasmid DNA (as obtained after ligation), efficiencies can be at least an order of magnitude lower. For making libraries, it is convenient to use commercially-available electrocompetent DH10B cells (Life Technologies) for the initial transformation, as these cells have a guaranteed transformation efficiency of $10^{10}$ cfu/µg of supercoiled plasmid DNA. Supercoiled DNA can be subsequently prepared and introduced into a non-commercial strain. For example, a general method for preparation of electrocompetent *E. coli* is as follows: (a) From a single colony or glycerol stock, inoculate a 5-mL LB starter culture containing the appropriate antibiotics (if any) and incubate at 37° C. with shaking at 250 rpm overnight; (b) From the starter culture, inoculate a 1-L 2×YT culture containing the appropriate antibiotics and grow to an optical density (OD) at 600 nm of 0.5; (c) Transfer culture to two ice-cold, 0.5-L GS3 tubes and centrifuge at 1° C. for 5 min at 10000 g. Decant the supernatant; (d) Resuspend the cells in 1 L of ice-cold 10% glycerol and centrifuge at 1° C. for 5 min at 7500 g. Decant the supernatant; (e) Repeat step 12d; and, (f) Quickly resuspend the cells in the residual 10% glycerol and keep them on ice. Transform the cells immediately or flash-freeze them on dry ice before storing them at about −80° C.

This section outlines the construction of a plasmid library of MjYRS variants and its introduction into the *E. coli* pREP/YC-JYCUA reporter strain. DNA oligonucleotide primers pBK-MjYRSN and pBK-MjYRSC (Table 3) were used to PCR-amplify MjYRS gene variant library fragments in four 100-µL PCR reactions. For example, standard PCR conditions for a 100-µL reaction are as follows: 10 µL 10' PCR buffer, 10 µL dNTPs (2 mM each), 4 µL each primer (10 µM each), ~10 ng template, and 1.5 µL DNA polymerase. Typically, 20 cycles of PCR were carried out using the following cycle: 95° C. for 1 min, 50° C. for 1 min, and 72° C. for 2 min. The DNA was purified using a PCR DNA purification kit. The purified PCR DNA was disgested using restriction enzymes, NdeI and PstI. Standard conditions for restriction enzyme digestion and CIP treatment are as described by, e.g., New England Biolabs. The digested PCR fragments were purified by agarose gel electrophoresis followed by gel extraction.

Standard agarose gel electrophoresis was performed using a 1% agarose gel with TAE buffer containing 0.5 µg/mL ethidium bromide. DNA was visualized under long-wavelength ultraviolet light, excised using a sterile razor blade, and removed from the gel slice by gel extraction. See, e.g., Sambrook, J. & Russell, D. W. (2001). *Molecular cloning: a laboratory manual*. 3rd edit. Cold Spring Harbor Laboratory Press, Cold Spring Harbor, N.Y.

The purified DNA was quantified by agarose gel electrophoresis. The vector pBK-JYA6 was disgested using restriction enzymes, NdeI and PstI. Optionally, a parent vector containing a "stuffer fragment" that is long enough to allow doubly- and singly-digested vector DNA fragments to be resolved can be used. Optionally, the vector is not treated with CIP; although CIP treatment increases the fraction of clones that contain insert, it significantly decreases transformation efficiency. The digested vector was purified by standard agarose gel electrophoresis followed by gel extraction. The purified DNA was quantified by agarose gel electrophoresis. The vector and insert DNA were ligated in a molar ratio of 1 to 1.5, respectively, using at least 10 µg of vector in a 300-µL reaction for ~12 hours at 16° C. Standard ligation reaction conditions are as described by New England Biolabs. Following ligation, a small amount of the reaction was analyzed by agarose gel electrophoresis to verify that all of the starting material has been converted to larger products. The ligation products were purified by extraction three times with 200 µL of phenol-chloroform and two times with 200 µL of chloroform, followed by ethanol precipitation. The DNA pellet was redissolved in 50 µL of water.

A pilot transformation of 25 µL of electrocompetent *E. coli* was carried out with 1 µL of the ligation product. A pilot transformation is useful to check the efficiency of the ligation reaction before proceeding with a large-scale transformation. Three ten-fold serial dilutions of the transformed cells were plated onto LB agar plates containing 35 µg/mL kanamycin and incubate at 37° C. overnight. Based on the number of colonies obtained, the expected library size was calculated. The plasmid DNA was miniprepped corresponding to 10-20 individual clones. The plasmids were restriction mapped and sequenced to verify that a high percentage (ideally, greater than about 70%, greater than about 80%, greater than about 90%, greater than 95% or more) of the clones contain insert and that the distribution of mutations within the library is not excessively biased.

If results from the pilot transformation are acceptable, a large-scale transformation is done. For example, the purified ligation products were mixed with 500 µL of electrocompetent cells (do not dilute). 55 µL aliquots of the mixture were distributed into ten cold 0.2-cm cuvettes and electroporate. Following each electroporation, 1 mL of SOC media was immediately added. Transformed cells were transferred to a 15-mL conical tube and allowed to recover with gentle shaking (225 rpm) at 37° C. for 1 hr. Recovered cells were transferred to 2 L of 2×YT media containing 35 µg/mL kanamycin in a 4-L shaker flask.

A 100-µL aliquot of the inoculated culture was immediately removed for use in estimating the number of independent transformants comprising the pR-C library. To estimate the number of independent transformants, three 10-fold serial dilutions of the 100-µL aliquot removed from the freshly-inoculated culture were made. 10 µL of each dilution (including the original aliquot) were plated onto a series of LB agar plates containing the appropriate antibiotics. Based on the resulting number of colonies, the total number of transformants in the culture was calculated.

The transferred cells were incubated at 37° C. overnight with shaking (250 rpm). The pBK plasmid DNA was maxiprepped from 500 mL of the library culture. The DNA was resdissolved in 200 µL of water. 200 µL of electrocompetent DH10B (pREP/YC-JYCUA) cells were transformed with 5 µL of the maxiprepped pBK supercoiled plasmid library DNA (~1-2 µg) in four 0.2-cm cuvettes. Following each electroporation, 1 mL of SOC media was immediately added. Transformed cells were transferred to a 15-mL conical tube and allowed to recover with gentle shaking (225 rpm) at 37° C. for 1 hr. Recovered cells were transferred to 1 L of 2×YT media containing 25 µg/mL tetracycline and 35 µg/mL kanamycin in a 2-L shaker flask. A 100-µL aliquot of the inoculated culture was immediately removed for use in estimating the number of independent transformants. This number is be at least about as large as the number of independent transformants obtained following library construction. The cells were incubated at 37° C. overnight with shaking (250 rpm).

A combination of selection and screening is used to identify MjYRS variants that have altered specificity with respect to the amino acid substrate (FIG. 6). A chloramphenicol-based selection is used to enrich variants that are active in the presence of an unnatural amino acid. A negative FACS-based screen is used to eliminate variants that are active in the absence of the unnatural amino acid. The following is an example of a method for using selection and FACS-based screening to direct the evolution of an aminoacyl-tRNA synthetase. 2 mL of *E. coli* (pREP/YC-JYCUA, pBK-lib) cells were pelleted by centrifugation at 10000 g for 1 min. The supernatant was discarded and the cells were resuspended in 1 mL of GMML media. To begin the first cycle of positive selection, the resuspended cells were used to inoculate 500 mL of GMML containing 25 µg/mL tetracycline, 35 µg/mL kanamycin, and 1 mM unnatural amino acid. *E. coli* grown in GMML media with sufficient aeration will saturate at an O.D. (600 nm) of ~1-2. The cells were incubated for 3 hr at 37° C. with shaking at 250 rpm. Chloramphenicol was added to a final concentration of 75 µg/mL and incubation continued until the cells reach stationary phase (~48 hr).

The optimal chloramphenicol concentration depends on the activity of synthetases in the initial library. Chloramphenicol is bacteriostatic rather than bactericidal, so selection efficiency should increase with increasing chloramphenicol concentration without loss of population diversity. In practice, the use of an arbitrarily high concentration of chloramphenicol often produces selection artifacts. Conversely, a chloramphenicol concentration that is too low can result in insufficient selection stringency. A chloramphenicol concentration of 75 µg/mL is used because it has been shown to be effective in enrichment experiments and lies somewhat below the $IC_{50}$ supported by the majority of the MjYRS variants that have been identified by directed evolution thus far. See Pastrnak, M., Magliery, T. J. & Schultz, P. G. (2000). *A new orthogonal suppressor tRNA/aminoacyl-tRNA synthetase pair for evolving an organism with an expanded genetic code.* Helv Chim Acta 83:2277-2286; Wang, L., Brock, A., Herberich, B. & Schultz, P. G. (2001). *Expanding the genetic code of Escherichia coli.* Science 292:498-500; Wang, L., Brock, A. & Schultz, P. G. (2002). *Adding L-3-(2naphthyl)alanine to the genetic code of E-coli.* J Am Chem Soc 124:1836-1837; and, Chin, J. W., Santoro, S. W., Martin, A. B., King, D. S., Wang, L. & Schultz, P. G. (2002). *Addition of p-Azido-L-phenylalanine to the genetic code of Escherichia coli.* J Am Chem Soc 124:9026-9027. Although it is possible that a different chloramphenicol concentration will be optimal for a given evolution experiment, about 75 µg/mL is an appropriate concentration for initial experiments.

To begin the second cycle of positive selection, a 500-µL aliquot of saturated culture was used from the first selection to inoculate a 100-mL GMML culture containing 25 µg/mL tetracycline, 35 µg/mL kanamycin, 75 µg/mL chloramphenicol, and 1 mM unnatural amino acid. The cells were incubated at 37° C. with shaking at 250 rpm until the cells reach stationary phase (~24-36 hr).

Figure 7:
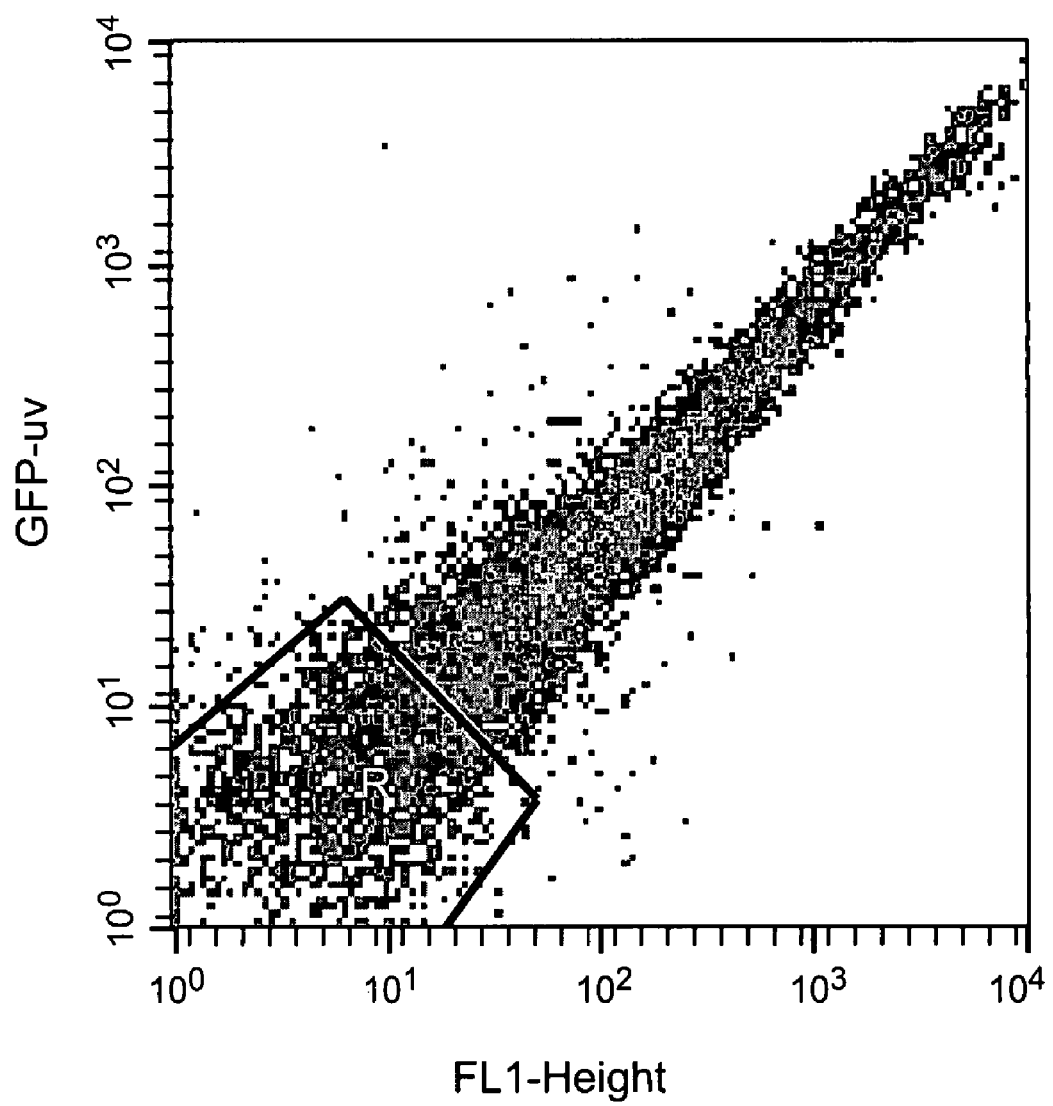
FIG. 7 illustrates FACS-based negative screening of MjYRS variants. The boxed events are collected, corresponding to cells producing little or no GFPuv. These cells, which were grown in the absence of the unnatural amino acid, contain MjYRS variants that cannot utilize as substrates any of the natural amino acids within *E. coli*.

To prepare for FACS-based negative screening, a 100-µL aliquot of cells were pelleted from the second cycle of positive selection by centrifugation at 10000 g for 1 min. The supernatant was discarded and the cells were resuspended in 100 μL of GMML media. The resuspended cells were used to inoculate a 25-mL GMML culture containing 25 μg/mL tetracycline, 35 μg/mL kanamycin, and 0.002% arabinose. An arabinose concentration of 0.002% has been optimized to allow controlled expression of the amber stop codon-containing T7 RNA polymerase gene within pREP/YC-JYCUA. This results in a robust fluorescence signal (in the presence of a suitably-charged suppressor tRNA) with minimal effects on the growth rate of the *E. coli* host. The cells were incubated at 37° C. with shaking at 250 rpm until the cells reach stationary phase (~24-36 hr). A 1-mL aliquot of the arabinose-induced cells was pelleted by centrifugation at 10000 g for 1 min. The cells were resuspended in 3 mL of phosphate-buffered saline (PBS). Using FACS, the cells were sorted, e.g., sort ~$10^7$-$10^8$ cells for the lack fluorescence (FIG. 7).

These experiments were carried out using a BDIS FACVantage cytometer with a TSO option. Laser excitation was performed using a Coherent Enterprise II 421 water-cooled argon ion laser, emitting 351 and 488 nm lines (30 and 250 mW, respectively). GFPuv is excited at 351 nm and produces emissions that are collected using a 519/20 nm bandpass filter. EYFP is excited at 488 nm and produces emissions that are collected using a 585/45 nm bandpass filter. Comparable systems can give similar results. The cytometer was specially configured to trigger on scatter from small particles. Both forward scatter (FSC) and median angle side scatter (SSC) are acquired on a log scale. The system was triggered by a SSC threshold to avoid the low level noise from FSC at high sensitivity. A 70 μm nozzle was used with a system pressure of ~30 psi. For example, cells are typically sorted at a rate of ~10,000/second.

The collected cells were diluted into 25 mL of LB media containing 25 μg/mL tetracycline and 35 μg/mL kanamycin and allowed to grow to saturation at 37° C. with shaking (250 rpm). A 100-μL aliquot of the amplified cells were pelleted by centrifugation at 10000 g for 1 min. The cells were resuspended in 100 μL of GMML. To begin the third cycle of positive selection, the resuspended cells were used to inoculate 25 mL of GMML containing 25 μg/mL tetracycline, 35 μg/mL kanamycin, and 1 mM unnatural amino acid. The cells were incubated for 3 hr at 37° C. with shaking at 250 rpm. Chloramphenicol was added to a final concentration of 75 μg/mL (the optimal chloramphenicol concentration depends on the activity of synthetase in the initial library as described above) and incubation continued until the cells reach stationary phase (~48 hr).

Figure 8:
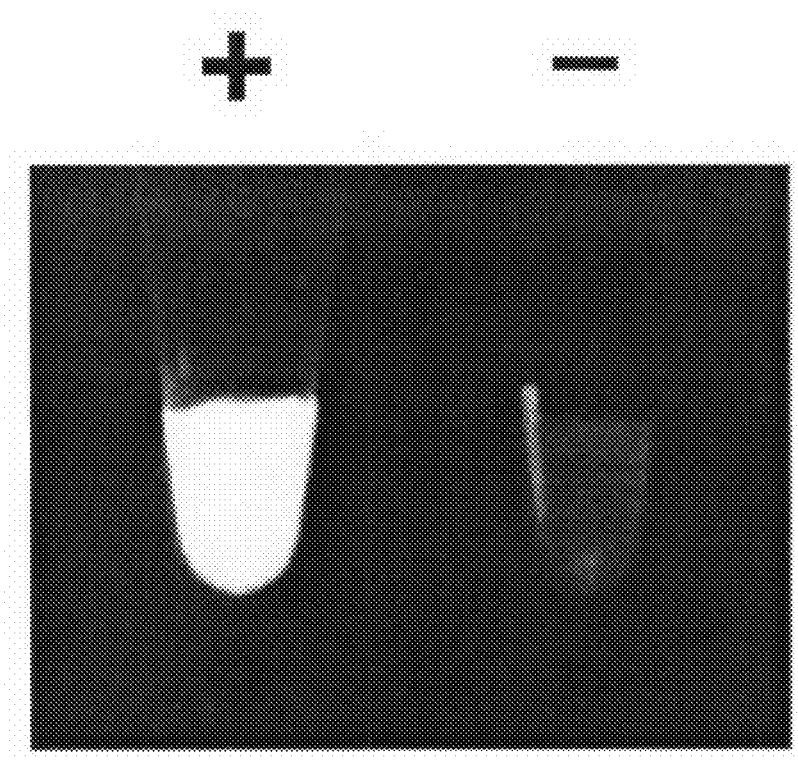
FIG. 8 illustrates long-wavelength ultraviolet illumination of cells containing an MjYRS variant that accepts only an unnatural amino acid substrate. Cells were grown in either the presence (+) or absence (−) of the unnatural amino acid.

The following steps outline the procedure by which the in vivo activity and specificity of individual synthetase selectants can be characterized fluorimetrically. Cells from the third cycle of positive selection were diluted into GMML to a density of ~50 cells/μL and 10-μL aliquots of the dilution were plated on eight GMML/agar plates containing 25 μg/mL tetracycline, 35 μg/mL kanamycin, 0.002% arabinose, 0 or 1 mM unnatural amino acid, and 0, 35, 75, or 100 μg/mL chloramphenicol. The plates were incubated at 37° C. for 48 hr. Using a handheld long-wavelength ultraviolet light, the number of fluorescent and non-fluorescent colonies were counted on each plate. If the evolution experiment is successful, there can be a greater number of fluorescent colonies on the plates containing the unnatural amino acid than on plates lacking the unnatural amino acid. From the plate containing the highest chloramphenicol concentration for which a significantly greater number of fluorescent colonies formed in the presence versus the absence of unnatural amino acid, 10-20 fluorescent colonies were picked. From each colony, 4 mL of GMML media containing 25 μg/mL tetracycline, 35 μg/mL kanamycin, and 0.002% arabinose was inoculated. 2 mL of each inoculated sample was transferred to a separate tube and the unnatural amino acid was added to a final concentration of 1 mM. All cultures were incubated at 37° C. with shaking (250 rpm) until the cells reach stationary phase (~24-36 hr). 200 μL of cells was pelleted from each culture by centrifugation at 10000 g for 1 min. The supernatant was decanted. At this point, a handheld long-wavelength ultraviolet light can be used to observe the visible fluorescence from each cell pellet (FIG. 8). Cells exhibiting no visible difference in fluorescence as a result of growth in the presence of the unnatural amino acid are likely to contain an MjYRS variant that accepts a natural amino acid; such cells need not be characterized further. The cells were resuspended in 1 mL of PBS. The cell optical density (at 600 nm) of each resuspended cell mixture was measured. 200 μL of each cell mixture was transferred to a cuvette and a fluorimeter was used to measure its fluorescence emission intensity at 505 nm with excitation at 396 nm. The cellular fluorescence was normalized by dividing the fluorescence intensity of each cell mixture by its $O.D._{600}$. The unnatural amino acid-dependent fluorescence corresponding to each MjYRS variant was determined by calculating the ratio of normalized cellular fluorescence values for cells grown in the presences versus the absence of the unnatural amino acid. An alternative option for analysis of synthetase activity and specificity is to measure the chloramphenicol $IC_{50}$ for cell growth on GMML agar plates in the presence versus the absence of the unnatural amino acid. See, e.g., Santoro, S. W., Wang, L., Herberich, B., King, D. S. & Schultz, P. G. (2002). *An efficient system for the evolution of aminoacyl-tRNA synthetase specificity. Nat Biotechnol,* 20:1044-1048.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 2

| SEQ ID # | Sequences | Notes | tRNA or RS |
|---|---|---|---|
| 1 | ATGGACGAATTTGAAATGATAAAGAGAAACACATCTGAAATTATCAGCGAGGAAGAG TTAAGAGAGGTTTTAAAAAAAGATGAAAAATCTGCTGGGATAGGTTTTGAACCAAGT | p-iPr-PheRS | RS |

TABLE 2-continued

| SEQ ID # | Sequences | Notes | tRNA or RS |
|---|---|---|---|
| | GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATGTGCTTATGGAAGTCCTTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATGGTTATCATTATCTTGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | | |
| 2 | ATGGACGAATTTGAAATGATAAAGAGAAACACATCTGAAATTATCAGCGAGGAAGAG<br>TTAAGAGAGGTTTTAAAAAAGATGAAAAATCTGCTCAGATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTCCTTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATTGTTCTCATTATTATGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | p-NH$_2$-PheRS(1) | RS |
| 3 | ATGGACGAATTTGAAATGATAAAGAGAAACACATCTGAAATTATCAGCGAGGAAGAG<br>TTAAGAGAGGTTTTAAAAAAGATGAAAAATCTGCTTACTATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTACGTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATCCGTTGCATTATGCTGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | p-NH$_2$-PheRS(2) | RS |
| 4 | ATGGACGAATTTGAAATGATAAAGAGAAACACATCTGAAATTATCAGCGAGGAAGAG<br>TTAAGAGAGGTTTTAAAAAAGATGAAAAATCTGCTCATATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTGAGTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATCGGCCGCATTATCCTGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | p-NH$_2$-PheRS(3a) | RS |
| 5 | ATGGACGAATTTGAAATGATAAAGAGAAACACATCTGAAATTATCAGCGAGGAAGAG<br>TTAAGAGAGGTTTTAAAAAAGATGAAAAATCTGCTTATATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTCCTTTCCAGCTTGATAAGGATTAT<br>ACACTGAATGTCTATAGATTGGCTTTAAAAACTACCTTAAAAAGAGCAAGAAGGAGT | p-NH$_2$-PheRS(3b) | RS |

| SEQ ID # | Sequences | Notes | tRNA or RS |
|---|---|---|---|
| | ATGGAACTTATAGCAAGAGAGGATGAAAATCCAAAGGTTGCTGAAGTTATCTATCCA<br>ATAATGCAGGTTAATCAGAGTCATTATGATGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | | |
| 6 | ATGGACGAATTTGAAATGATAAAGAGAAACACATCTGAAATTATCAGCGAGGAAGAG<br>TTAAGAGAGGTTTTAAAAAAAGATGAAAAATCTGCTTCGATAGGTTTTGAACCAAGT<br>GGTAAAATACATTTAGGGCATTATCTCCAAATAAAAAAGATGATTGATTTACAAAAT<br>GCTGGATTTGATATAATTTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTACGTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATACGTATCATTATGCTGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | O-Allyl-TyrRS(1)#<br>#see also OAY-<br>RS(1) in Santoro et al.<br>(2002) Nature Bio-<br>technology, 20:1044-<br>1048 | RS |
| 7 | ATGGACGAATTTGAAATGATAAAGAGAAACACATCTGAAATTATCAGCGAGGAAGAG<br>TTAAGAGAGGTTTTAAAAAAAGATGAAAAATCTGCTCCTATAGGTTTTGAACCAAGT<br>GGTAAAATACATTTAGGGCATTATCTCCAAATAAAAAAGATGATTGATTTACAAAAT<br>GCTGGATTTGATATAATTTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTATGTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATAATACGCATTATGGGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | O-Allyl-TyrRS(3)*<br>* see also OAY-<br>RS(5) in Santoro et al.<br>(2002) Nature Bio-<br>technology, 20:1044-<br>1048 | RS |
| 8 | ATGGACGAATTTGAAATGATAAAGAGAAACACATCTGAAATTATCAGCGAGGAAGAG<br>TTAAGAGAGGTTTTAAAAAAAGATGAAAAATCTGCTTACGATAGGTTTTGAACCAAGT<br>GGTAAAATACATTTAGGGCATTATCTCCAAATAAAAAAGATGATTGATTTACAAAAT<br>GCTGGATTTGATATAATTTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTCATTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATCAGACTCATTATGAGGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA<br>GCATACTGCCCAGCTGGAGTTGTTGAAGGAAATCCAATAATGGAGATAGCTAAATAC<br>TTCCTTGAATATCCTTTAACCATAAAAAGGCCAGAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTA | O-Allyl-TyrRS(4)<br>see also OAY-RS (3)<br>in Santoro et al. (2002)<br>Nature Biotechnology,<br>20:1044-1048 | RS |
| 9 | ATGGACGAATTTGAAATGATAAAGAGAAACACATCTGAAATTATCAGCGAGGAAGAG<br>TTAAGAGAGGTTTTAAAAAAAGATGAAAAATCTGCTCATATAGGTTTTGAACCAAGT<br>GGTAAAATACATTTAGGGCATTATCTCCAAATAAAAAAGATGATTGATTTACAAAAT<br>GCTGGATTTGATATAATTTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTAAGTTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATCCGTGTCATTATCATGGCGTTGATGTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA | p-Br-PheRS | RS |

TABLE 2-continued

| SEQ ID # | Sequences | Notes | tRNA or RS |
|---|---|---|---|
| | GCATACTGCCCAGCTGGAGTTGTTGAAGGAAATCCAATAATGGAGATAGCTAAATAC TTCCTTGAATATCCTTTAACCATAAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | | |
| 10 | ATGGACGAATTTGAAATGATAAAGAGAAACACATCTGAAATTATCAGCGAGGAAGAG TTAAGAGAGGTTTTAAAAAAGATGAAAAATCTGCTGCTATAGGTTTTGAACCAAGT GGTAAAATACATTTAGGGCATTATCTCCAAATAAAAAAGATGATTGATTTACAAAAT GCTGGATTTGATATAATTATATTGTTGGCTGATTTACACGCCTATTTAAACCAGAAA GGAGAGTTGGATGAGATTAGAAAATAGGAGATTATAACAAAAAAGTTTTTGAAGCA ATGGGGTTAAAGGCAAAATATGTTTATGGAAGTCGGTTCCAGCTTGATAAGGATTAT ACACTGAATGTCTATAGATTGGCTTTAAAAACTACCTTAAAAAGAGCAAGAAGGAGT ATAATGCAGGTTAATGTGATTCATTATGATGGCGTTGATGTTGCAGTTGGAGGGATG GAGCAGAGAAAAATACACATGTTAGCAAGGGAGCTTTTACCAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | p-Az-PheRS(1) | RS |
| 11 | ATGGACGAATTTGAAATGATAAAGAGAAACACATCTGAAATTATCAGCGAGGAAGAG TTAAGAGAGGTTTTAAAAAAGATGAAAAATCTGCTGGGATAGGTTTTGAACCAAGT GGTAAAATACATTTAGGGCATTATCTCCAAATAAAAAAGATGATTGATTTACAAAAT GCTGGATTTGATATAATTATATTGTTGGCTGATTTACACGCCTATTTAAACCAGAAA GGAGAGTTGGATGAGATTAGAAAATAGGAGATTATAACAAAAAAGTTTTTGAAGCA ATGGGGTTAAAGGCAAAATATGTTTATGGAAGTACTTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATACGTATTATTATGCTGGCGTTGATGTTGCAGTTGGAGGGATG GAGCAGAGAAAAATACACATGTTAGCAAGGGAGCTTTTACCAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | p-Az-PheRS(3) | RS |
| 12 | ATGGACGAATTTGAAATGATAAAGAGAAACACATCTGAAATTATCAGCGAGGAAGAG TTAAGAGAGGTTTTAAAAAAGATGAAAAATCTGCTCTGAGTTTTGAACCAAGT GGTAAAATACATTTAGGGCATTATCTCCAAATAAAAAAGATGATTGATTTACAAAAT GCTGGATTTGATATAATTATATTGTTGGCTGATTTACACGCCTATTTAAACCAGAAA GGAGAGTTGGATGAGATTAGAAAATAGGAGATTATAACAAAAAAGTTTTTGAAGCA ATGGGGTTAAAGGCAAAATATGTTTATGGAAGTCCGTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATCAGATTCATTCTAGTGGCGTTGATGTTGCAGTTGGAGGGATG GAGCAGAGAAAAATACACATGTTAGCAAGGGAGCTTTTACCAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | p-Az-PheRS(5) | RS |
| 13 | ATGGACGAATTTGAAATGATAAAGAGAAACACATCTGAAATTATCAGCGAGGAAGAG TTAAGAGAGGTTTTAAAAAAGATGAAAAATCTGCTGGTATAGGTTTTGAACCAAGT GGTAAAATACATTTAGGGCATTATCTCCAAATAAAAAAGATGATTGATTTACAAAAT GCTGGATTTGATATAATTATATTGTTGGCTGATTTACACGCCTATTTAAACCAGAAA GGAGAGTTGGATGAGATTAGAAAATAGGAGATTATAACAAAAAAGTTTTTGAAGCA ATGGGGTTAAAGGCAAAATATGTTTATGGAAGTTCCTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATACGAGTCATTATCTGGGCGTTGATGTTGCAGTTGGAGGGATG GAGCAGAGAAAAATACACATGTTAGCAAGGGAGCTTTTACCAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | Aminoacyl tRNA synthetase for the incorporation of p-benzoyl-L-phenylalanine (p-BpaRS(H6)) | RS |

TABLE 2-continued

| SEQ ID # | Sequences | Notes | tRNA or RS |
|---|---|---|---|
| 14 | ATGGACGAATTTGAAATGATAAAGAGAAACACATCTGAAATTATCAGCGAGGAAGAG TTAAGAGAGGTTTTAAAAAAGATGAAAAATCTGCTACGATAGGTTTTGAACCAAGT GGTAAAATACATTTAGGGCATTATCTCCAAATAAAAAAGATGATTGATTTACAAAT GCTGGATTTGATATAATTTATATTGTTGGCTGATTTACACGCCTATTTAAACCAGAAA GGAGAGTTGGATGAGATTAGAAAAATAGGAGATTATAACAAAAAAGTTTTTGAAGCA ATGGGGTTAAAGGCAAAATATGTTTATGGAAGTAATTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATCCGCTTCATTATCAGGGCGTTGATGTTGCAGTTGGAGGGATG GAGCAGAGAAAAATACACATGTTAGCAAGGGAGCTTTTACCAAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | Aminoacyl tRNA synthetase for the incorportaion of p-azido-phenylalanine (p-Az-PheRS(3)) | RS |
| 15 | ATGGACGAATTTGAAATGATAAAGAGAAACACATCTGAAATTATCAGCGAGGAAGAG TTAAGAGAGGTTTTAAAAAAGATGAAAAATCTGCTACGATAGGTTTTGAACCAAGT GGTAAAATACATTTAGGGCATTATCTCCAAATAAAAAAGATGATTGATTTACAAAT GCTGGATTTGATATAATTTATATTGTTGGCTGATTTACACGCCTATTTAAACCAGAAA GGAGAGTTGGATGAGATTAGAAAAATAGGAGATTATAACAAAAAAGTTTTTGAAGCA ATGGGGTTAAAGGCAAAATATGTTTATGGAAGTCTGTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATCCTCTTCATTATGAGGGCGTTGATGTTGCAGTTGGAGGGATG GAGCAGAGAAAAATACACATGTTAGCAAGGGAGCTTTTACCAAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | Aminoacyl tRNA synthetase for the incorporation of p-azido-phenylalanine (p-Az-PheRS(6)) | RS |
| 16 | ATGGACGAATTTGAAATGATAAAGAGAAACACATCTGAAATTATCAGCGAGGAAGAG TTAAGAGAGGTTTTAAAAAAGATGAAAAATCTGCTCTTATAGGTTTTGAACCAAGT GGTAAAATACATTTAGGGCATTATCTCCAAATAAAAAAGATGATTGATTTACAAAT GCTGGATTTGATATAATTTATATTGTTGGCTGATTTACACGCCTATTTAAACCAGAAA GGAGAGTTGGATGAGATTAGAAAAATAGGAGATTATAACAAAAAAGTTTTTGAAGCA ATGGGGTTAAAGGCAAAATATGTTTATGGAAGTACTTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATCCGGTTCATTATCAGGGCGTTGATGTTGCAGTTGGAGGGATG GAGCAGAGAAAAATACACATGTTAGCAAGGGAGCTTTTACCAAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | Aminoacyl tRNA synthetase for the incorporation of p-azido-phenylalanine (p-Az-PheRS(20) | RS |
| 17 | ATGGACGAATTTGAAATGATAAAGAGAAACACATCTGAAATTATCAGCGAGGAAGAG TTAAGAGAGGTTTTAAAAAAGATGAAAAATCTGCTACTATAGGTTTTGAACCAAGT GGTAAAATACATTTAGGGCATTATCTCCAAATAAAAAAGATGATTGATTTACAAAT GCTGGATTTGATATAATTTATATTGTTGGCTGATTTACACGCCTATTTAAACCAGAAA GGAGAGTTGGATGAGATTAGAAAAATAGGAGATTATAACAAAAAAGTTTTTGAAGCA ATGGGGTTAAAGGCAAAATATGTTTATGGAAGTTCGTTCCAGCTTGATAAGGATTAT ACACTGAATGTCTATAGATTGGCTTTAAAAACTACCTTAAAAAGAGCAAGAAGGAGT ATGGAACTTATAGCAAGAGAGGATGAAAATCCAAAGGTTGCTGAAGTTATCTATCCA ATAATGCAGGTTAATCCACTGCATTATCAGGGCGTTGATGTTGCAGTTGGAGGGATG GAGCAGAGAAAAATACACATGTTAGCAAGGGAGCTTTTACCAAAAAAGGTTGTTTGT ATTCACAACCCTGTCTTAACGGGTTTGGATGGAGAAGGAAAGATGAGTTCTTCAAAA GGGAATTTTATAGCTGTTGATGACTCTCCAGAAGAGATTAGGGCTAAGATAAAGAAA GCATACTGCCCAGCTGGAGTTGTTGAAGGAAATCCAATAATGGAGATAGCTAAATAC TTCCTTGAATATCCTTTAACCATAAAAGGCCAGAAAATTTGGTGGAGATTTGACA GTTAATAGCTATGAGGAGTTAGAGAGTTTATTTAAAAATAAGGAATTGCATCCAATG GATTTAAAAAATGCTGTAGCTGAAGAACTTATAAAGATTTTAGAGCCAATTAGAAAG AGATTA | Aminoacyl tRNA synthetase for the incorporation of p-azido-phenylalanine (p-Az-PheRS(24)) | RS |
| 18 | MDEFEMIKRNTSEIISEEELREVLKKDEKSALIGFEPSGKIHLGHYLQIKKMIDLQN AGFDIIILLADLHAYLNQKGELDEIRKIGDYNKKVFEAMGLKAKYVYGSEFQLDKDY TLNVYRLALKTTLKRARRSMELIAREDENPKVAEVIYPIMQVNGCHYRGCDVAVGGM EQRKIHMLARELLPKKVVCIHNPVLTGLDGEGKMSSSKGNFIAVDDSPEEIRAKIKK | LW1RS | RS |

TABLE 2-continued

| SEQ ID # | Sequences | Notes | tRNA or RS |
|---|---|---|---|
| | AYCPAGVVEGNPIMEIAKYFLEYPLTIKRPEKFGGDLTVNSYEELESLFKNKELHPM DLKNAVAEELIKILEPIRKRL | | |
| 19 | MDEFEMIKRNTSEIISEEELREVLKKDEKSALIGFEPSGKIHLGHYQIKKMDLQN AGFDIIILLADLHAYLNQKGELDEIRKIGDYNKKVFEAMGLKAKYVYGSEFQLDKDY TLNVYRLALKTTLKRARRSMELIAREDENPKVAEVIYPIMQVNGTHYRGVDVAVGGM EQRKIHMLARELLPKKVVCIHNPVLTGLDGEGKMSSSKGNFIAVDDSPEEIRAKIKK AYCPAGVVEGNPIMEIAKYFLEYPLTIKRPEKFGGDLTVNSYEELESLFKNKELHPM DLKNAVAEELIKILEPIRKRL | LW5RS | RS |
| 20 | MDEFEMIKRNTSEIISEEELREVLKKDEKSAAIGFEPSGKIHLGHYLQIKKMIDLQN AGFDIIILLADLHAYLNQKGELDEIRKIGDYNKKVFEAMGLKAKYVYGSEFQLDKDY TLNVYRLALKTTLKRARRSMELIAREDENPKVAEVIYPIMQVNGGHYLGVDVIVGGM EQRKIHMLARELLPKKVVCIHNPVLTGLDGEGKMSSSKGNFIAVDDSPEEIRAKIKK AYCPAGVVEGNPIMEIAKYFLEYPLTIKRPEKFGGDLTVNSYEELESLFKNKELHPM DLKNAVAEELIKILEPIRKRL | LW6RS | RS |
| 21 | CCGGCGGUAGUUCAGCAGGGCAGAACGGCGGACUCUAAAUCCGCAUGGCGCUGGUUC AAAUCCGGCCCGCCGGACCA | mutRNA$^{Tyr}_{CUA}$ | tRNA |

What is claimed is:

1. A method of producing a protein in a cell with a keto amino acid at a specified position, the method comprising:
  growing, in an appropriate medium, the cell, where the cell comprises a nucleic acid that comprises at least one selector codon and encodes a protein; and,
  providing the keto amino acid, wherein the keto amino acid is a derivative of a tyrosine or a phenylalanine amino acid;

wherein the cell further comprises:
  an orthogonal tRNA (O-tRNA) that functions in the cell and recognizes the selector codon; and,
  an orthogonal aminoacyl-tRNA synthetase (O-RS) comprising an amino acid sequence selected from SEQ ID NO: 18 or a conservative variation thereof comprising at least 90% identity with SEQ ID NO: 18;
  wherein the ORS further comprises as Ala or Leu at a position corresponding to position 32 and comprises Gly at a position corresponding to position 158 compared to wild type tyrosy 1 tRNA synthetase from *Methanococcus jannaschii*; and incorporating the keto amino acid into the specified position in the protein during translation of the nucleic acid with the at least one selector codon, thereby producing the protein.

2. The method of claim 1, wherein the O-RS comprises an amino acid sequence which comprises any one of SEQ ID NO: 18-20.

3. The method of claim 1, wherein the O-tRNA comprises or is encoded by a polynucleotide sequence as set forth in SEQ ID NO: 21, or a complementary polynucleotide sequence thereof.

4. The method of claim 1, wherein the cell is a non-eukaryotic cell.

5. The method of claim 4, wherein the non-eukaryotic cell is an *E. coli* cell.

6. The method of claim 1, wherein the keto amino acid is p-acetyl-L-phenylalanine.

7. The method of claim 1, wherein the keto amino acid is a para-substituted derivative of phenylalanine or tyrosine.

* * * * *